United States Patent
Treu et al.

(10) Patent No.: US 7,981,880 B2
(45) Date of Patent: Jul. 19, 2011

(54) 3-(AMINOMETHYLIDEN) 2-INDOLINONE DERIVATES AND THEIR USE AS CELL PROLIFERATION INHIBITORS

(75) Inventors: Matthias Treu, Vienna (AT); Andreas Mantoulidis, Vienna (AT); Ulrike Tontsch-Grunt, Baden (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/297,970

(22) PCT Filed: Apr. 23, 2007

(86) PCT No.: PCT/EP2007/053959
§ 371 (c)(1),
(2), (4) Date: Dec. 23, 2008

(87) PCT Pub. No.: WO2007/122219
PCT Pub. Date: Nov. 1, 2007

(65) Prior Publication Data
US 2009/0105216 A1    Apr. 23, 2009

(30) Foreign Application Priority Data
Apr. 24, 2006   (EP) .................................... 06112985

(51) Int. Cl.
| | |
|---|---|
| A61K 31/553 | (2006.01) |
| A61K 31/5377 | (2006.01) |
| A61K 31/454 | (2006.01) |
| A61K 31/404 | (2006.01) |
| C07D 267/10 | (2006.01) |
| C07D 413/12 | (2006.01) |
| C07D 401/12 | (2006.01) |
| C07D 209/34 | (2006.01) |

(52) U.S. Cl. ................ 514/211.15; 514/235.2; 514/323; 514/418; 540/544; 544/144; 546/201; 548/486

(58) Field of Classification Search ............. 514/211.15, 514/418, 323, 235.2; 548/486; 546/201; 544/144; 540/544
See application file for complete search history.

(56) References Cited

U.S. PATENT DOCUMENTS
6,638,965 B2   10/2003   Walter et al.

FOREIGN PATENT DOCUMENTS
| CA | 2 381 821 A1 | 3/2001 |
| WO | 01/16130 A1 | 3/2001 |
| WO | 01/27080 A2 | 4/2001 |
| WO | 02/36564 A1 | 5/2002 |

OTHER PUBLICATIONS

Joel R. Huff, HIV Protease: A Novel Chemotherapeutic Target for AIDS, 1991, Journal of Medicinal Chemistry, vol. 34, No. 8, pp. 2305-2314.*
Lala et al., Role of nitric oxide in tumor progression: Lessons from experimental tumors, 1998, Cancer and Metastasis Reviews, 17(1), 91-106.*
Golub et al., Molecular Classification of Cancer: Class Discovery and Class Prediction by Gene Expression Monitoring, 1999, Science, vol. 286, 531-537.*
International Search Report for PCT/EP2007/053959 mailed Aug. 27, 2007.

* cited by examiner

*Primary Examiner* — Kamal Saeed
*Assistant Examiner* — Kristin Bianchi
(74) *Attorney, Agent, or Firm* — Michael P. Morris; Mary-Ellen M. Devlin

(57) ABSTRACT

The present invention encompasses compounds of general formula (1) wherein $R^1$, $R^2$, $R^3$ and X are defined as in claim 1, which are suitable for the treatment of diseases characterised by excessive or abnormal cell proliferation, and the use thereof for preparing a pharmaceutical composition having the above-mentioned properties.

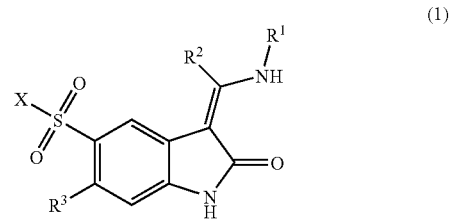

(1)

7 Claims, No Drawings

3-(AMINOMETHYLIDEN) 2-INDOLINONE DERIVATES AND THEIR USE AS CELL PROLIFERATION INHIBITORS

This application is a national phase entry under 35 U.S.C. 371 of international application PCT/EP2007/053959, filed Apr. 23, 2007, which claims priority to European Application No. EP 06112985.4, filed Apr. 24, 2006, each of which is hereby incorporated by reference in its entirety.

The present invention relates to new indolinones of general formula (1)

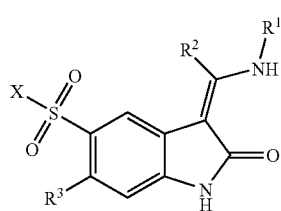

(1)

wherein the groups $R^1$, $R^2$, $R^3$ and X have the meanings given in the claims and specification, the isomers thereof, processes for preparing these indolinones and their use as pharmaceutical compositions.

Indolinones are generally known as inhibitors of kinases, particularly with an inhibiting effect on cyclin/CDK complexes. International Patent Application WO 01/27080 describes inter alia indolinones which carry alkoxysulphonyl or alkylaminosulphonyl groups in the 5-position, WO 01/16130 includes indolinones which are substituted by an alkoxy group in the 5-position, or indolinones that carry a methylenedioxy bridge in the 5- and 6-position. WO02/36654 describes indolinones which are substituted by a sulphonylamino group in the 5-position.

The aim of the present invention is to indicate new active substances that can be used for the prevention and/or treatment of diseases characterised by excessive or abnormal cell proliferation.

DETAILED DESCRIPTION OF THE INVENTION

It has been found that, surprisingly, compounds of general formula (1) wherein the groups $R^1$, $R^2$, $R^3$ and X have the meanings given hereinafter, act as inhibitors of specific cell cycle kinases. Thus the compounds according to the invention may be used for example for the treatment of diseases associated with the activity of specific cell cycle kinases and characterised by excessive or abnormal cell proliferation.

The present invention relates to compounds of general formula (1)

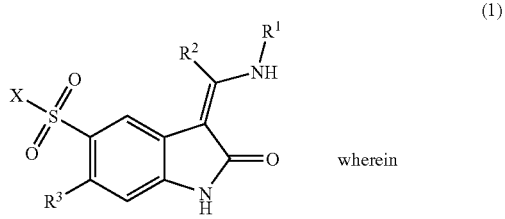

(1)

wherein

X denotes —$NR^4R^5$ or —$OR^5$; and
$R^1$ denotes a group, optionally substituted by one or more $R^6$, selected from among $C_{6-15}$aryl and 5-15 membered heteroaryl; and
$R^2$ denotes a group, optionally substituted by one or more $R^6$, selected from among $C_{3-10}$cycloalkyl, 3-8 membered heterocycloalkyl, $C_{6-15}$aryl and 5-15 membered heteroaryl; and
$R^3$ denotes hydrogen or a group selected from among $R^a$, $R^b$ and $R^a$ substituted by one or one or more identical or different $R^b$ and/or $R^c$; and
$R^4$ denotes hydrogen or $C_{1-6}$alkyl; and
$R^5$ denotes hydrogen or a group, optionally substituted by one or more $R^a$ and/or $R^b$, selected from among $C_{1-6}$alkyl, $C_{3-10}$cycloalkyl, $C_{4-14}$cycloalkylalkyl, 3-8 membered heterocycloalkyl, 4-14 membered heterocycloalkylalkyl and 6-16 membered heteroarylalkyl; or
$R^4$ and $R^5$ together with the nitrogen atom to which they are linked form a heterocycloalkyl or heteroaryl ring, wherein this ring may optionally also contain one or more identical or different additional heteroatoms, selected from among nitrogen, oxygen and sulphur, and which may optionally be substituted by one or more identical or different suitable $R^e$ and/or $R^f$; and
$R^6$ denotes a group selected from among $R^a$, $R^b$ and $R^a$ substituted by one or one or more identical or different $R^b$ and/or $R^c$; and
each $R^a$ is independently of one another selected from among $C_{1-6}$alkyl, $C_{3-10}$cycloalkyl, $C_{4-16}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl; and
each $R^b$ is a suitable group, each independently selected from among =O, —$OR^c$, $C_{1-3}$haloalkyloxy, —$OCF_3$, =S, —$SR^c$, =$NR^c$, =$NOR^c$, —$NR^cR^c$, halogen, —$CF_3$, —CN, —NC, —OCN, —SCN, —$NO_2$, —$S(O)R^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)_2NR^cR^c$, —$C(O)R^c$, —$C(O)OR^c$, —$C(O)NR^cR^c$, —$CN(R^f)NR^cR^c$, —CN(OH)$R^c$, —CN(OH)NR$^c$R$^c$, —$OC(O)R^c$, —$OC(O)OR^c$, —OC(O)NR$^c$R$^c$, —$OCN(R^f)NR^cR^c$, —$N(R^f)C(O)R^c$, —$N(R^f)C(S)R^c$, —$N(R^f)S(O)_2R^c$, —$N(R^f)C(O)OR^c$, —$N(R^f)C(O)NR^cR^c$, —[N($R^f$)C(O)]$_2$R$^c$, —N[C(O)]$_2$R$^c$, —N[C(O)]$_2$OR$^c$, —[N($R^f$)C(O)]$_2$OR$^c$ and —$N(R^f)CN(R^f)NR^cR^c$; and
each $R^c$ independently of one another is hydrogen or a group optionally substituted by one or more identical or different $R^d$ and/or $R^e$ selected from among $C_{1-6}$alkyl, $C_{3-10}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl; and
each $R^d$ independently of one another is hydrogen or a group optionally substituted by one or more identical or different $R^e$ and/or $R^f$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl; and
each $R^e$ is a suitable group, each independently selected from among =O, —$OR^f$, $C_{1-3}$haloalkyloxy, —$OCF_3$, =S, —$SR^f$, =$NR^f$, =$NOR^f$, —$NR^fR^f$, halogen, —$CF_3$, —CN, —NC, —OCN, —SCN, —$NO_2$, —$S(O)R^f$, —$S(O)_2R^f$, —$S(O)_2OR^f$, —$S(O)NR^fR^f$, —$S(O)_2NR^fR^f$, —$OS(O)R^f$, —$OS(O)_2R^f$, —$OS(O)_2OR^f$, —$OS(O)_2NR^fR^f$, —$C(O)R^f$, —$C(O)OR^f$, —$C(O)NR^fR^f$, —$CN(R^g)NR^fR^f$, —CN(OH)$R^f$, —CN(OH)NR$^f$R$^f$, —$OC(O)R^f$, —$OC(O)OR^f$, —OC(O)NR$^f$R$^f$, —$OCN(R^g)NR^fR^f$, —$N(R^g)C(O)R^f$, —$N(R^g)C(S)R^f$, —N(R$^g$)S(O)$_2$R$^f$, —N(R$^d$)C(O)OR$^f$, —N(R$^g$)C(O)NR$^f$R$^f$, and —N(R$^g$)CN(R$^f$)NR$^f$R$^f$; and each R$^f$ independently of one another is hydrogen or a group optionally substituted by one or more identical or different R$^g$ selected from among C$_{1-6}$alkyl, C$_{3-8}$cycloalkyl, C$_{4-11}$cycloalkylalkyl, C$_{6-10}$aryl, C$_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl; and each R$^g$ independently of one another is hydrogen, C$_{1-6}$alkyl, C$_{3-8}$cycloalkyl, C$_{4-11}$cycloalkylalkyl, C$_{6-10}$aryl, C$_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl, optionally in the form of the tautomers, the racemates, the enantiomers, the diastereomers and the mixtures thereof, and optionally the pharmacologically acceptable acid addition salts thereof, with the proviso that 3-Z-[1-(4-(piperidin-1-yl-methyl)-anilino)-1-phenyl-methylene]-5-(N-buty-N-methyl-aminosulphonyl)-2-indolinone and 3-Z-[1-(4-(dimethylaminomethyl)-anilino)-1-phenyl-methylene]-5-aminosulphonyl-2-indolinone are excluded.

(A) Aspects Relating to R$^1$ (A1) In one aspect the invention relates to compounds of general formula (1), wherein R$^1$ denotes a phenyl group optionally substituted by one or more R$^6$.

(A2) In another aspect the invention relates to compounds of general formula (1), wherein R$^1$ denotes a phenyl group substituted by an R$^6$ in the 4-position (para position).

(A3) In another aspect the invention relates to compounds of general formula (1), wherein R$^1$ denotes a phenyl group substituted by an R$^6$ in the 4-position (para position) and R$^6$ denotes a group of formula —(CH$_2$)$_x$—NR$^7$R$^8$, wherein R$^7$ and R$^8$ each independently have the meanings of R$^4$ and R$^5$ and x denotes 0 or 1.

(A4) In another aspect the invention relates to compounds of general formula (1), wherein R$^1$ denotes a phenyl group substituted by an R$^6$ in the 4-position (para position) and R$^6$ denotes a group of formula —(CH$_2$)$_x$—NR$^7$R$^8$, wherein R$^7$ denotes hydrogen or C$_{1-3}$ alkyl, and R$^8$ denotes a group, optionally substituted by one or more R$^a$ and/or R$^b$, selected from among C$_{1-3}$ alkyl, C$_{3-10}$cycloalkyl, C$_{3-6}$ cycloalkyl-methyl, 3-8 membered heterocycloalkyl, 3-8 membered heterocycloalkyl-methyl and 5 or 6 membered heteroarylmethyl.

(A5) In another aspect the invention relates to compounds of general formula (1), wherein R$^1$ denotes a phenyl group substituted by an R$^6$ in the 4-position (para position) and R$^6$ denotes a group of formula —(CH$_2$)$_x$—NR$^7$R$^8$, wherein R$^7$ and R$^8$ together with the nitrogen atom to which they are linked form a 3- to 6 membered heterocycloalkyl or 5 or 6 membered heteroaryl ring, wherein this ring may optionally also contain one or two identical or different additional heteroatoms selected from among nitrogen, oxygen and sulphur, and which may optionally be substituted by a group selected from among R$^e$ and R$^f$.

(B) Aspects Relating to R$^2$ (B1) In another aspect the invention relates to compounds of general formula (1), wherein R$^2$ denotes phenyl, cyclohexyl or pyridyl.

(B2) In another aspect the invention relates to compounds of general formula (1), wherein R$^2$ denotes unsubstituted phenyl.

(C) Aspects Relating to X (C1) In another aspect the invention relates to compounds of general formula (1), wherein X denotes —NR$^4$R$^5$.

(C2) In another aspect the invention relates to compounds of general formula (1), wherein X denotes —NR$^4$R$^5$, wherein R$^4$ denotes hydrogen or C$_{1-3}$ alkyl, and R$^5$ denotes a group, optionally substituted by one or more R$^a$ and/or R$^b$, selected from among C$_{1-3}$ alkyl, C$_{3-10}$cycloalkyl, C$_{3-6}$ cycloalkyl-methyl, 3-8 membered heterocycloalkyl, 3-8 membered heterocycloalkyl-methyl and 5 or 6 membered heteroarylmethyl.

(C3) In another aspect the invention relates to compounds of general formula (1), wherein X denotes —NR$^4$R$^5$, wherein R$^4$ and R$^5$ together with the nitrogen atom to which they are linked form a 3- to 6 membered heterocycloalkyl or 5 or 6 membered heteroaryl ring, wherein this ring may optionally also contain one or two identical or different additional heteroatoms selected from among nitrogen, oxygen and sulphur, and which may optionally be substituted by a group selected from among R$^e$ and R$^f$.

All the above-mentioned aspects (A1) to (A5) for R$^1$, (B1) and (B2) for R$^2$ and (C1) to (C3) for X may be combined with one another as desired.

The Table below shows preferred combinations of various aspects of the compounds of formula 1 according to the invention:

| embodiment | R$^1$ | R$^2$ | X |
|---|---|---|---|
| I-1 | A1 | B1 | C1 |
| I-2 | A2 | B1 | C1 |
| I-3 | A3 | B1 | C1 |
| I-4 | A4 | B1 | C1 |
| I-5 | A5 | B1 | C1 |
| I-6 | A1 | B2 | C1 |
| I-7 | A2 | B2 | C2 |
| I-8 | A3 | B2 | C3 |
| I-9 | A4 | B2 | C2 |
| I-10 | A5 | B2 | C3 |

In another aspect the invention relates to compounds of general formula (1) as pharmaceutical compositions.

In another aspect the invention relates to compounds of general formula (1) for preparing a pharmaceutical composition with an antiproliferative activity.

In another aspect the invention relates to a pharmaceutical preparation, containing as active substance one or more compounds of general formula (1) or the physiologically acceptable salts thereof optionally in combination with conventional excipients and/or carriers.

In another aspect the invention relates to the use of compounds of general formula (1) for preparing a pharmaceutical composition for the treatment and/or prevention of cancer, infections, inflammations and autoimmune diseases.

In another aspect the invention relates to a pharmaceutical preparation comprising a compound of general formula (1)

and at least one other cytostatic or cytotoxic active substance, different from formula (1), optionally in the form of the tautomers, the racemates, the enantiomers, the diastereomers and the mixtures thereof, and optionally the pharmacologically acceptable acid addition salts thereof.

DEFINITIONS

As used herein the following definitions apply, unless stated otherwise.

By alkyl substituents are meant in each case saturated, unsaturated, straight-chain or branched aliphatic hydrocarbon groups (alkyl group) and this includes both saturated alkyl groups and unsaturated alkenyl and alkynyl groups. Alkenyl substituents are in each case straight-chain or branched, unsaturated alkyl groups, which have at least one double bond. By alkynyl substituents are meant in each case straight-chain or branched, unsaturated alkyl groups, which have at least one triple bond.

Heteroalkyl represents unbranched or branched aliphatic hydrocarbon chains which contain 1 to 3 heteroatoms, while each of the available carbon and heteroatoms in the heteroalkyl chain may optionally each be substituted independently and the heteroatoms independently of one another are selected from among O, N, P, PO, $PO_2$, S, SO and $SO_2$ (e.g. dimethylaminomethyl, dimethylaminoethyl, dimethylaminopropyl, diethylaminomethyl, diethylaminoethyl, diethylaminopropyl, 2-diisopropylaminoethyl, bis-2-methoxyethylamino, [2-(dimethylamino-ethyl)-ethyl-amino]-methyl, 3-[2-(dimethylamino-ethyl)-ethyl-amino]-propyl, hydroxymethyl, 2-hydroxyethyl, 3-hydroxypropyl, methoxy, ethoxy, propoxy, methoxymethyl, 2-methoxyethyl).

Haloalkyl refers to alkyl groups wherein one or more hydrogen atoms are replaced by halogen atoms. Haloalkyl includes both saturated alkyl groups and unsaturated alkenyl and alkynyl groups, such as for example —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —CI=$CH_2$, —C≡C—$CF_3$, —$CHFCH_2CH_3$ and —$CHFCH_2CF_3$.

Halogen refers to fluorine, chlorine, bromine and/or iodine atoms.

By cycloalkyl is meant a mono- or polycyclic ring, wherein the ring system may be a saturated ring but also an unsaturated, non-aromatic ring or a spiro compound, which may optionally also contain double bonds, such as for example cyclopropyl, cyclopropenyl, cyclobutyl, cyclobutenyl, cyclopentyl, cyclopentenyl, cyclohexyl, cyclohexenyl, cycloheptanyl, cycloheptenyl, norbornyl, norbornenyl, indanyl, adamantyl, spiroheptanyl and spiro[4.2]heptanyl.

Cycloalkylalkyl includes a non-cyclic alkyl group wherein a hydrogen atom bound to a carbon atom is replaced by a cycloalkyl group.

Aryl relates to monocyclic or bicyclic rings with 6-12 carbon atoms such as for example phenyl and naphthyl.

Arylalkyl includes a non-cyclic alkyl group wherein a hydrogen atom bound to a carbon atom is replaced by an aryl group.

By heteroaryl are meant mono- or polycyclic rings which contain, instead of one or more carbon atoms, one or more heteroatoms, which may be identical or different, such as e.g. nitrogen, sulphur or oxygen atoms. Examples include furyl, furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heteroaryl groups are indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, quinolinyl, phthalazinyl, quinazolinyl and benzotriazinyl, indolizinyl, oxazolopyridinyl, imidazopyridinyl, naphthyridinyl, indolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl-N-oxide, pyrimidinyl-N-oxide, pyridazinyl-N-oxide, pyrazinyl-N-oxide, quinolinyl-N-oxide, indolyl-N-oxide, indolinyl-N-oxide, isoquinolyl-N-oxide, quinazolinyl-N-oxide, quinoxalinyl-N-oxide, phthalazinyl-N-oxide, imidazolyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, tetrazolyl-N-oxide, benzothiopyranyl-S-oxide and benzothiopyranyl-S,S-dioxide.

Heteroarylalkyl encompasses a non-cyclic alkyl group wherein a hydrogen atom bound to a carbon atom is replaced by a heteroaryl group.

Heterocycloalkyl relates to saturated or unsaturated, non-aromatic mono-, polycyclic or bridged polycyclic rings or spiro compounds comprising 3-12 carbon atoms, which carry heteroatoms, such as nitrogen, oxygen or sulphur, instead of one or more carbon atoms. Examples of such heterocyclyl groups are tetrahydrofuranyl, pyrrolidinyl, pyrrolinyl, imidazolidinyl, imidazolinyl, pyrazolidinyl, pyrazolinyl, piperidinyl, piperazinyl, indolinyl, isoindolinyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, tetrahydropyranyl, tetrahydrothienyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-S-oxide, tetrahydrothienyl-S,S-dioxide, homothiomorpholinyl-S-oxide, 6-aza-bicyclo[3.2.1]octane, 2-oxa-5-azabicyclo[2.2.1]heptane, 2-aza-bicyclo[2.2.1]hept-5-ene, 8-oxa-3-aza-bicyclo[3.2.1]octane, 3,8-diaza-bicyclo[3.2.1]octane, 2,5-diaza-bicyclo[2.2.1]heptane, 3,8-diaza-bicyclo[3.2.1]octane, 3,9-diaza-bicyclo[4.2.1]nonane and 2,6-diaza-bicyclo[3.2.2] nonane.

Heterocycloalkylalkyl relates to a non-cyclic alkyl group wherein a hydrogen atom bound to a carbon atom is replaced by a heterocycloalkyl group.

Preparation of the Compounds According to the Invention

Method A—2-oxo-2,3-dihydro-1H-indole-5-sulphonyl Chloride

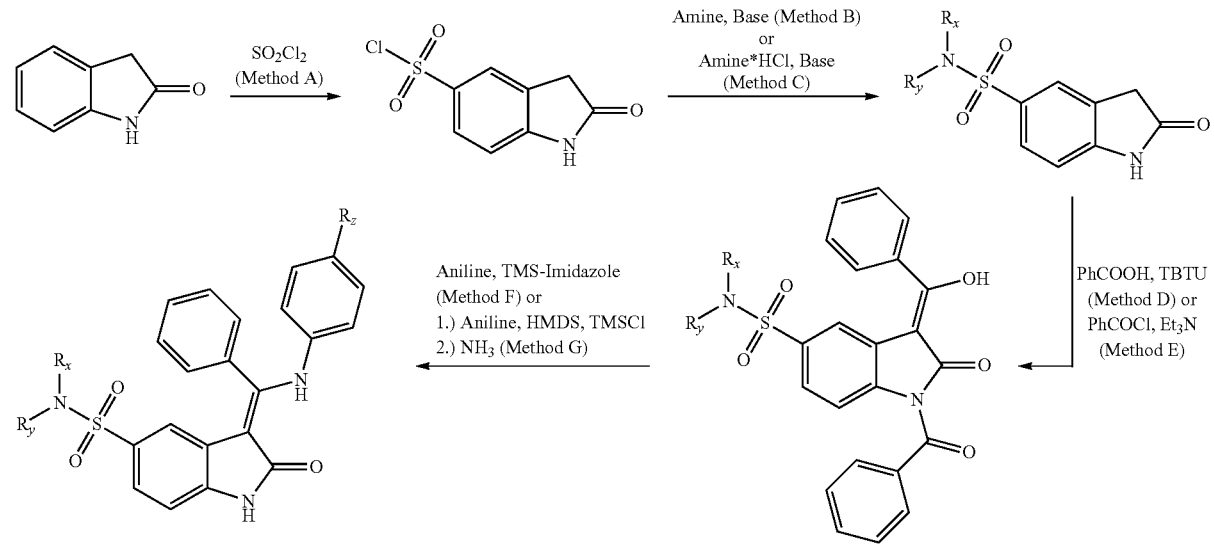

2-indolinone (5 g, 37.6 mmol) is added batchwise at 0° C. to chlorosulphonic acid (13 mL), stirred for 30 min at this temperature and then for 16 h at RT. The reaction mixture is slowly poured onto 200 mL of ice water, the precipitate is filtered off, digested with water until the washing water has a neutral reaction and dried in vacuo at 45° C. Yield: 7.65 g tate is filtered off, stirred in 0.1 N HCl (150 mL) for 30 min at RT, filtered off again, digested with water and dried at 45° C. in vacuo. Yield: 13.8 g If during the preparation of analogous compounds the product is not precipitated from the reaction solution in the form of a solid, this solution is diluted with dichloromethane, washed with 0.1 N HCl, water and saturated saline solution, dried on $Na_2SO_4$, filtered and evaporated down. The crude product may optionally be purified by chromatography.

| # | structure | educt |
|---|---|---|
| A.1 | (structure) | (structure) |
| A.2 | (structure) | (structure) Quallich. G. J.; Morrissey, P.M. Synthesis 1993, 51-53 |

Method B—2-oxo-2,3-dihydro-1H-indole-5-sulphonic Acid cyclopropyl-methylamide Cyclopropylmethylamine (5 mL, 57.6 mmol) is added dropwise within 5 min at 0° C. to a mixture of 2-oxo-2,3-dihydro-1H-indole-5-sulphonyl chloride (12 g, 51.8 mmol) and triethylamine (10.8 mL, 77.7 mmol) in anhydrous dichloromethane (150 mL) and stirred for 1.5 h at RT. The precipi-

Method C—2-oxo-2,3-dihydro-1H-indole-5-sulphonic Acid Ethylamide

The preparation of the sulphonamides starting from amine hydrochlorides is carried out analogously to Method B using 3 equivalents of triethylamine.

| # | structure | educt |
|---|-----------|-------|
| B.1 | *N-(pyridin-2-ylmethyl)-2-oxoindoline-5-sulfonamide* | 2-oxoindoline-5-sulfonyl chloride |
| B.2 | *N-ethyl-6-ethoxy-2-oxoindoline-5-sulfonamide* | 6-ethoxy-2-oxoindoline-5-sulfonyl chloride |
| B.3 | *N-cyclopentyl-2-oxoindoline-5-sulfonamide* | 2-oxoindoline-5-sulfonyl chloride |
| B.4 | *tert-butyl 4-((2-oxoindoline-5-sulfonamido))piperidine-1-carboxylate* | 2-oxoindoline-5-sulfonyl chloride |
| B.5 | *N-(1-methylpiperidin-4-yl)-2-oxoindoline-5-sulfonamide* | 2-oxoindoline-5-sulfonyl chloride |

| # | structure | educt |
|---|---|---|
| B.6 | 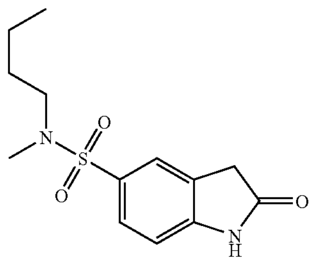 | |
| C.1 | 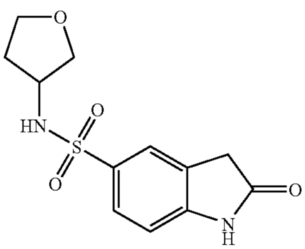 | |

Method D—1-benzoyl-3-[1-hydroxy-1-phenylmeth-(Z)-ylidene]-2-oxo-2,3-dihydro-1H-indole-5-sulphonic Acid Cyclopropylmethylamide Benzoic acid (3.6 g, 29.5 mmol) and TBTU (9.8 g, 30.5 mmol) are stirred in anhydrous DMF (10 mL) for 10 min at RT, combined with 2-oxo-2,3-dihydro-1H-indole-5-sulphonic acid-cyclopropylmethylamide (3.88 g, 14.5 mmol) and stirred for 5 min at RT. N-Ethyldiisopropylamine (20 mL) is added and the mixture is stirred for 16 h at 45° C. The reaction mixture is poured onto 0.1 N HCl (150 mL), the precipitated solid is filtered off, digested with water and dried in vacuo at 45° C. Yield: 6.9 g If during the preparation of analogous compounds the product is not precipitated from the aqueous phase in the form of a solid, this aqueous phase is quantitatively extracted with EtOAc. The combined organic phases are washed with 0.1 N HCl, water, dilute $NaHCO_3$ solution and saturated saline solution, dried on $Na_2SO_4$, filtered and evaporated down. The crude product may optionally be purified by chromatography.

| # | structure | educt |
|---|---|---|
| D.1 | 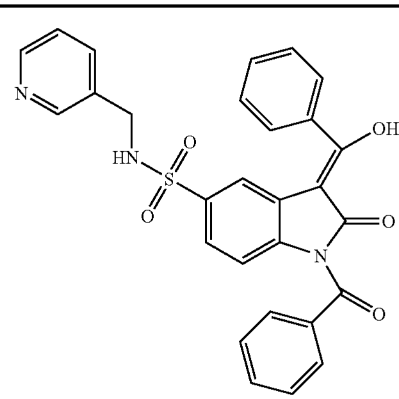 | |

-continued

| # | structure | educt |
|---|-----------|-------|
| D.2 | 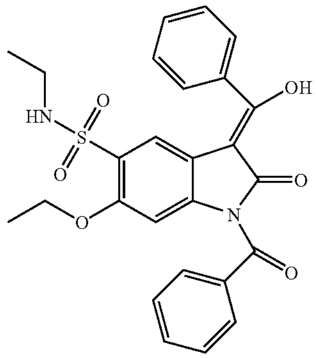 | |
| D.3 | 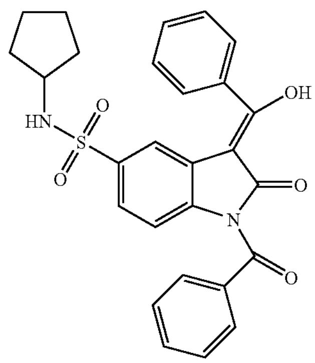 | |
| D.4 | 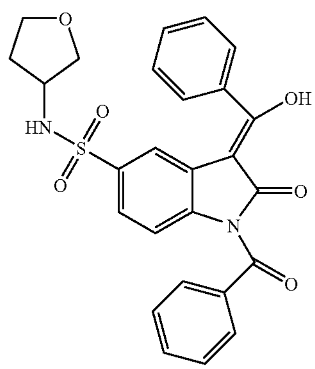 | |
| D.5 | 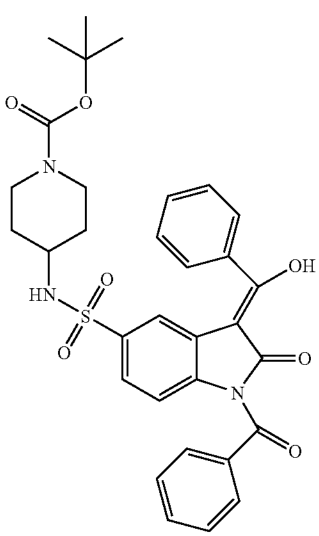 | |

-continued

| # | structure | educt |
|---|-----------|-------|
| D.6 | 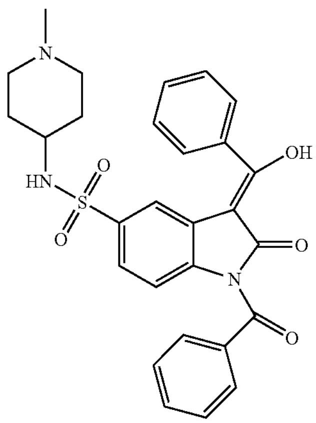 | |
| D.7 | 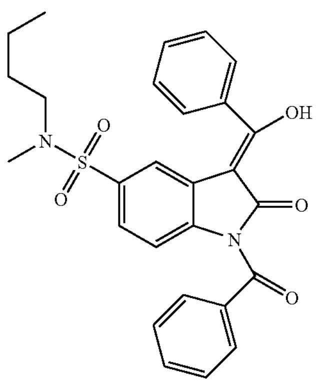 | |
| D.8 | 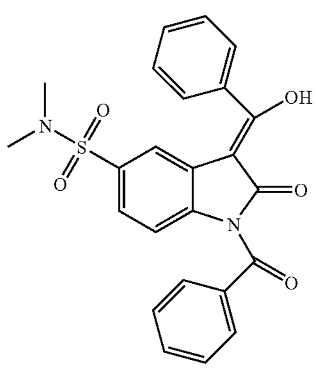 | |
| D.9 | 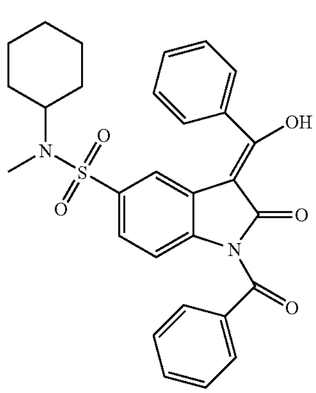 | |

-continued

| # | structure | educt |
|---|---|---|
| D.10 | 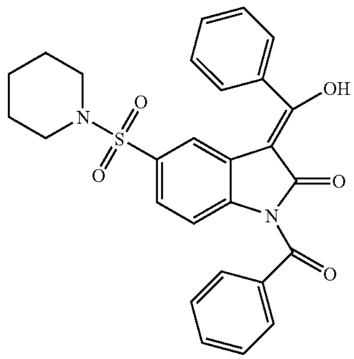 | |
| D.11 | 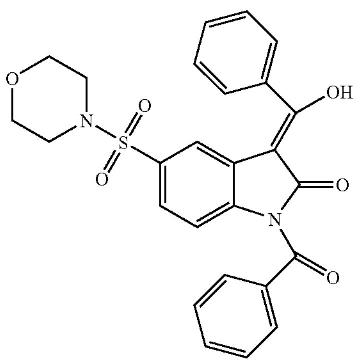 | |
| D.12 | 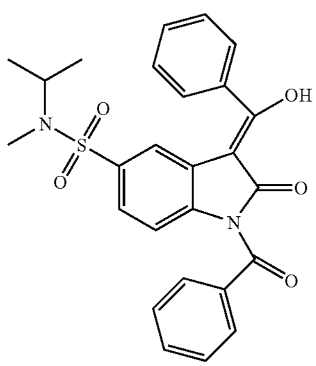 | |
| D.13 | 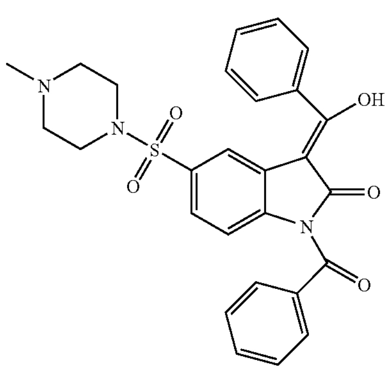 | |

Method E—1-benzoyl-3-[1-hydroxy-1-phenylmeth-(Z)-ylidene]-2-oxo-2,3-dihydro-1H-indole-5-sulphonic acid-(3-dimethylaminopropyl)amide Benzoic acid chloride (410 µL, 3.53 mmol) is added to a mixture of 2-oxo-2,3-dihydro-1H-indole-5-sulphonic acid-(3-dimethylamino-propyl)amide (500 mg, 1.68 mmol), triethylamine (2.43 mL) and DMAP (20 mg) in anhydrous dichloromethane (5 mL) and the mixture is stirred for 16 h at RT. The working up is carried out analogously to Method D.
Yield: 511 mg

Method F—3-[1-[4-(4-methylpiperazin-1-yl)phenylamino]-1-phenylmeth-(Z)-ylidene]-2-oxo-2,3-dihydro-1H-indole-5-sulphonic Acid Cyclopropylmethylamide 1-benzoyl-3-[1-hydroxy-1-phenylmeth-(Z)-ylidene]-2-oxo-2,3-dihydro-1H-indole-5-sulphonic acid cyclopropylmethylamide (75 mg, 0.16 mmol), 4-(4-methylpiperazino)aniline (33.2 mg, 0.17 mmol) and trimethylsilylimidazole (47 µL, 0.32 mmol) are stirred in anhydrous THF (500 µL) for 15 min at 170° C. in the microwave. The product is filtered off, digested repeatedly with THF and dried at 45° C. in vacuo.
Yield: 30 mg If in analogous reactions on a scale greater than 100 mg the product is not precipitated as a solid from the reaction solution, the latter is diluted with EtOAC, washed with 0.1 N HCl, water and saturated saline solution, dried on $Na_2SO_4$, filtered and evaporated down. The crude product may optionally be purified by chromatography.

Method G—tert-butyl 4-[2-oxo-3-[1-phenyl-1-(4-pyrrolidin-1-ylmethylphenylamino)-meth-(Z)-ylidene]-2,3-dihydro-1H-indole-5-sulphonylamino]-piperidine-1-carboxylate tert.-Butyl 4-[1-benzoyl-3-[1-hydroxy-1-phenylmeth-(Z)-ylidene]-2-oxo-2,3-dihydro-1H-indole-5-sulphonylamino]-piperidine-1-carboxylate (800 mg, 0.8 mmol), 4-pyrrolidin-1-ylmethylphenylamine (280 mg, 1.59 mmol), chlorotrimethylsilane (206 µL, 1.62 mmol) and hexamethyldisilazane (337 µL, 1.59 mmol) are refluxed in anhydrous dioxane (8 mL) for 16 h with stirring. The reaction mixture is evaporated down and purified by column chromatography.
Yield: 240 mg If in analogous reactions on a scale below 100 mg the product is not precipitated as a solid from the reaction solution, the latter is evaporated down, the residue is taken up in DMSO, DMF or NMP and purified by preparative HPLC/MS.

If in analogous reactions on a scale greater than 100 mg the product is not precipitated as a solid from the reaction solution, the latter is diluted with EtOAC, washed with 0.1 N HCl, water and saturated saline solution, dried on $Na_2SO_4$, filtered and evaporated down. The crude product may optionally be purified by chromatography.

According to Method F—ethanesulphonic acid [6-ethoxy-2-oxo-3-[1-phenyl-1-(4-pyrrolidin-1-ylmethylphenylamino)meth-(Z)-ylidene]-2,3-dihydro-1H-indol-5-yl]amide Ethanesulphonic acid [6-ethoxy-3-[1-hydroxy-1-phenylmeth-(Z)-ylidene]-2-oxo-2,3-dihydro-1H-indol-5-yl]amide (100 mg, 0.2 mmol), 4-pyrrolidin-1-ylmethylphenylamine (107 mg, 0.61 mmol) and trimethylsilylimidazole (148 µL, 1.01 mmol) are stirred in anhydrous THF (400 µL) for 15 min at 170° C. in the microwave. The mixture is diluted with DMSO, DMF or NMP, purified by preparative HPLC/MS and the fractions obtained are lyophilised. Yield: 2.5 mg If in analogous reactions on a scale greater than 100 mg the product is not precipitated as a solid from the reaction solution, the latter is diluted with EtOAC, washed with 0.1 N HCl, water and saturated saline solution, dried on $Na_2SO_4$, filtered and evaporated down. The crude product may optionally be purified by chromatography.

According to Method G—2-methylpropane-1-sulphonic acid [3-[1-(3-methoxy-4-pyrrolidin-1-ylmethyl-phenylamino)-1-phenylmeth-(Z)-ylidene]-2-oxo-2,3-dihydro-1H-indol-5-yl]amide 2-methylpropane-1-sulphonic acid [3-[1-hydroxy-1-phenylmeth-(Z)-ylidene]-2-oxo-2,3-dihydro-1H-indol-5-yl]amide (230 mg, 0.48 mmol), 3-methoxy-4-pyrrolidin-1-ylmethyl-phenylamine (198 mg, 0.96 mmol), chlorotrimethylsilane (122 µL, 0.96 mmol) and hexamethyldisilazane (203 µL, 0.96 mmol) are stirred in anhydrous THF (5 mL) for 30 min at 150° C. in the microwave. The mixture is diluted with DMSO, DMF or NMP, purified by preparative HPLC/MS and the fractions obtained are lyophilised.
Yield: 18 mg If in analogous reactions on a scale greater than 100 mg the product is not precipitated as a solid from the reaction solution, the latter is diluted with EtOAC, washed with 0.1 N HCl, water and saturated saline solution, dried on $Na_2SO_4$, filtered and evaporated down. The crude product may optionally be purified by chromatography.

Reaction mixtures on the gram scale are processed at reflux temperature.

In the event that in analogous reactions the acyl group has not been cleaved from the indolinone-nitrogen in the course of the reaction, the saponification is carried out with ammonia solution or aqueous sodium hydroxide solution.

EXAMPLES 1-5

| Ex. | structure | $t_{Ret}$ [min] | $UV_{max}$ [nm] | $[M + H]^+$ |
|---|---|---|---|---|
| 1 | 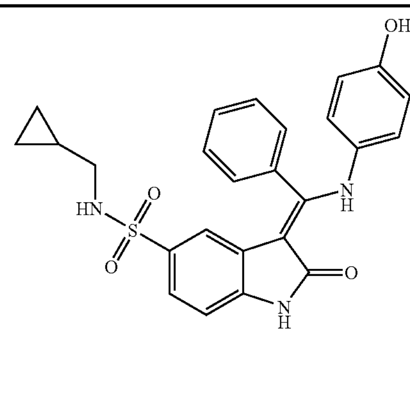 | 1.81 | 368 | 462.3 |

-continued
| Ex. | structure | $t_{Ret}$ [min] | $UV_{max}$ [nm] | $[M + H]^+$ |
|---|---|---|---|---|
| 2 | 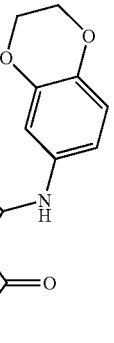 | 2.01 | 376 | 504.2 |
| 3 | 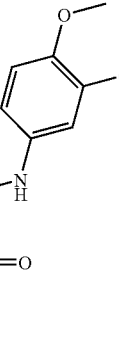 | 2.10 | 371 | 510.2 |
| 4 | 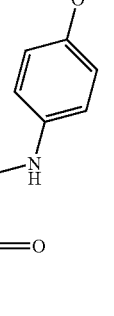 | 2.03 | 374 | 476.2 |
| 5 | 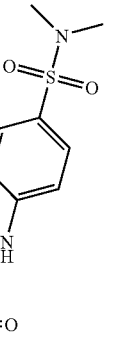 | 2.036 | 387 | 541.3 |

Method J—1-(4-nitrobenzyl)pyrrolidine

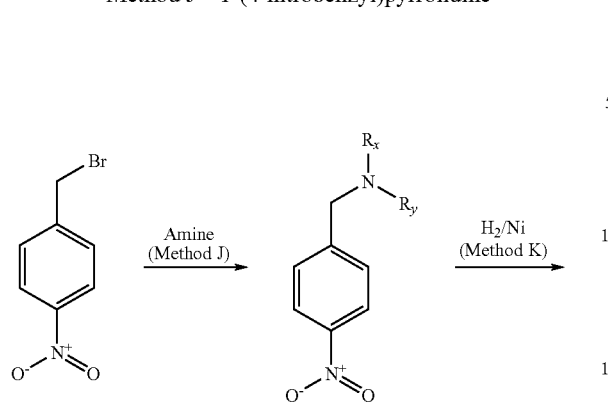

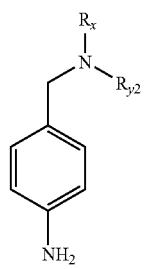

4-nitrobenzylbromide (25 g, 115 mmol) is added batchwise to a solution of pyrrolidine (24 mL, 290 mmol) in anhydrous THF (50 mL) and the mixture is stirred for 16 h at RT. The reaction mixture is evaporated down, taken up in EtOAC (300 mL), washed with saturated $NH_4Cl$ solution, water and saturated saline solution, dried on sodium sulphate, filtered and evaporated down. Yield: 16.96 g

| # | structure | educt |
|---|-----------|-------|
| J.1 | 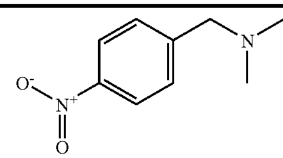 | |
| J.2 | 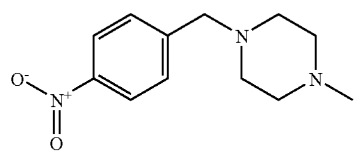 | |

Method K—4-pyrrolidin-1-ylmethylphenylamine 1-(4-nitrobenzyl)pyrrolidine (16.96 g, 82.2 mmol) in anhydrous THF (50 mL) is combined with Raney nickel (5 g) and hydrogenated for 21 h under a hydrogen pressure of 7.5 bar at RT. Optionally further catalyst is metered in and the hydrogen pressure is readjusted as it falls. The reaction mixture is filtered, evaporated down, combined with toluene (3×200 mL) and evaporated down again. Yield: 14.46 g

| # | structure | educt |
|---|-----------|-------|
| K.1 | 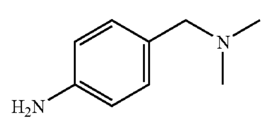 | |
| K.2 | 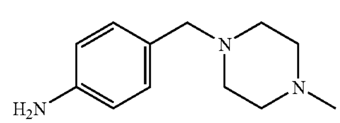 | |

Method S—(2-chloro-4-nitrophenyl)methanol

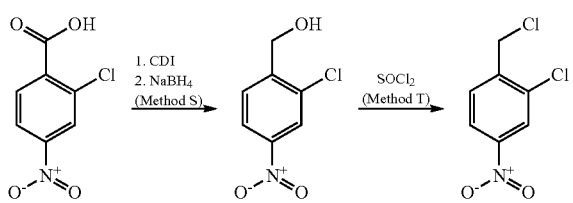

Method T—2-chloro-1-chloromethyl-4-nitrobenzene (2-chloro-4-nitrophenyl)methanol (19 g, 101 mmol) is stirred in a mixture of anhydrous dichloromethane (400 mL), thionyl chloride (15 mL) and DMF (1 mL) for 2 h at boiling temperature. The reaction mixture is evaporated down, the residue is taken up in EtOAc (250 mL), washed with water (5×150 mL) and saturated saline solution (150 mL), dried on sodium sulphate, filtered and evaporated down.

Yield: 20.4 g

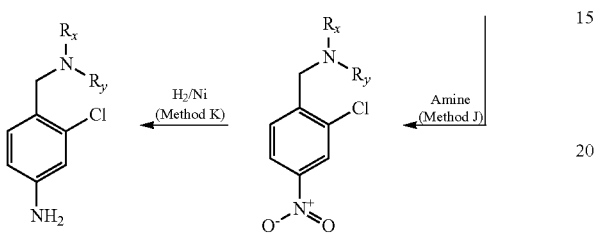

N,N'-carbonyldiimidazole (19.91 g, 122 mmol) is added batchwise at RT to 2-chloro-4-nitrobenzoic acid (25 g, 90% purity, 111 mmol) in anhydrous THF (420 mL) and the mixture is stirred for 1 h. At 15-20° C. sodium borohydride (13.09 g, 346 mmol) in water (85 mL) is added dropwise and the mixture is stirred for 16 h at RT. The reaction mixture is adjusted to pH 1 with 6 N HCl and extracted exhaustively with EtOAc. The combined organic phases are washed with 15% potassium carbonate solution (2×150 mL) and saturated saline solution (150 mL), dried on sodium sulphate, filtered and evaporated down. Yield: 20.6 g

| # | structure | educt |
|---|-----------|-------|
| T.1 | ![structure] | ![educt] |

| # | structure | educt |
|---|-----------|-------|
| S.1 | ![structure] | ![educt] |
| S.2 | ![structure] | ![educt] |

1-(2-chloro-4-nitrobenzyl)pyrrolidine is prepared according to Method J.

| # | structure | educt |
|---|-----------|-------|
| J.3 | 2-chloro-4-nitrobenzyl-pyrrolidine | 2-chloro-4-nitrobenzyl chloride |
| J.4 | N,N-dimethyl-(2-chloro-4-nitrobenzyl)amine | 2-chloro-4-nitrobenzyl chloride |
| J.5 | 1-(2-methoxy-4-nitrobenzyl)pyrrolidine | 2-methoxy-4-nitrobenzyl chloride |

3-chloro-4-pyrrolidin-1-ylmethylphenylamine is prepared according to Method K.

| # | structure | educt |
|---|-----------|-------|
| K.3 | 3-chloro-4-pyrrolidin-1-ylmethylphenylamine | 1-(2-chloro-4-nitrobenzyl)pyrrolidine |
| K.4 | 3-chloro-4-(N,N-dimethylaminomethyl)phenylamine | N,N-dimethyl-(2-chloro-4-nitrobenzyl)amine |
| K.5 | 3-methoxy-4-pyrrolidin-1-ylmethylphenylamine | 1-(2-methoxy-4-nitrobenzyl)pyrrolidine |

3-[1-(4-aminomethylphenylamino)-1-phenylmeth-(Z)-ylidene]-2-oxo-2,3-dihydro-1H-indole-5-sulphonamide derivatives are prepared according to Method G.

EXAMPLES 6-35

| # | structure | $t_{Ret}$ [min] | $UV_{max}$ [nm] | $[M + H]^+$ |
|---|---|---|---|---|
| 6 | 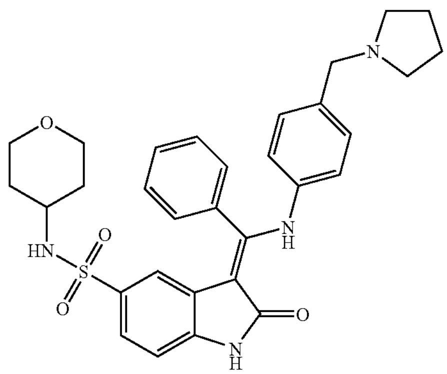 | 1.63 | 377 | 559.2 |
| 7 | 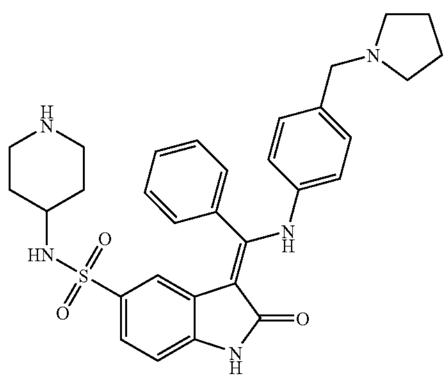 | 1.34 | 378 | 558.3 |
| 8 | 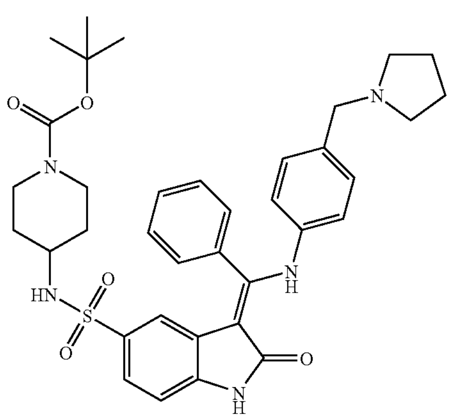 | 1.81 | 377 | 658.3 |

-continued
| # | structure | $t_{Ret}$ [min] | $UV_{max}$ [nm] | $[M + H]^+$ |
|---|---|---|---|---|
| 9 | 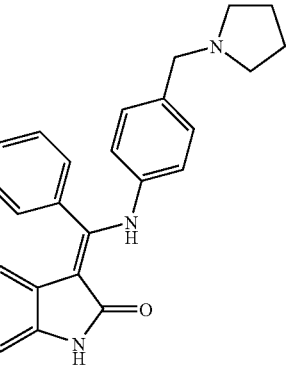 | 0.13 | 379 | 514.2 |
| 10 | 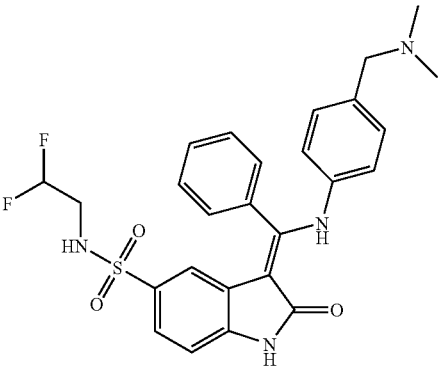 | 1.45 | 378 | 513.3 |
| 11 | 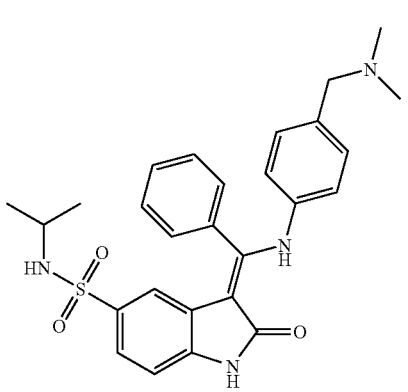 | 1.40 | 378 | 491.2 |
| 12 | 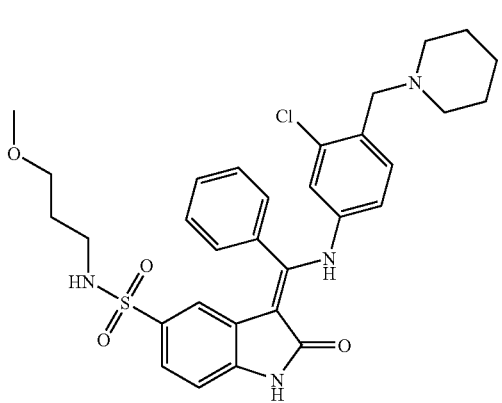 | 1.57 | 379 | 595.2 |

-continued
| # | structure | $t_{Ret}$ [min] | $UV_{max}$ [nm] | $[M+H]^+$ |
|---|---|---|---|---|
| 13 | 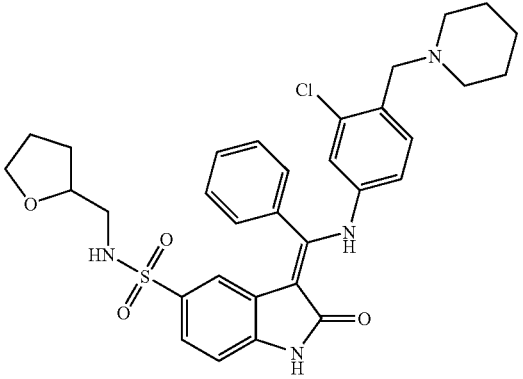 | 1.56 | 381 | 607.2 |
| 14 | 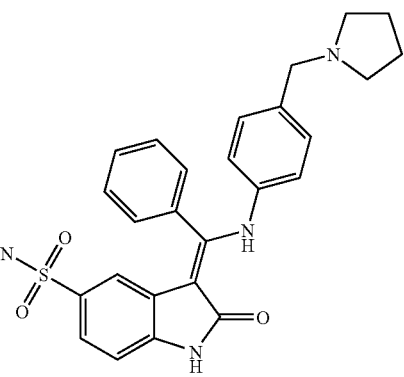 | 0.12 | 375 | 475.2 |
| 15 | 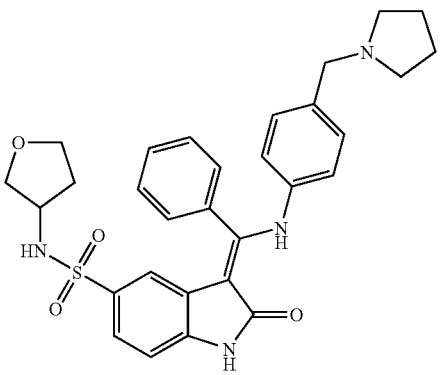 | 1.41 | 376 | 559.2 |
| 16 | 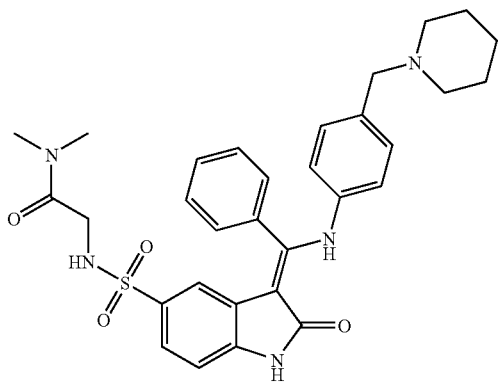 | 1.38 | 378 | 574.2 |

-continued
| # | structure | $t_{Ret}$ [min] | $UV_{max}$ [nm] | $[M + H]^+$ |
|---|---|---|---|---|
| 17 | 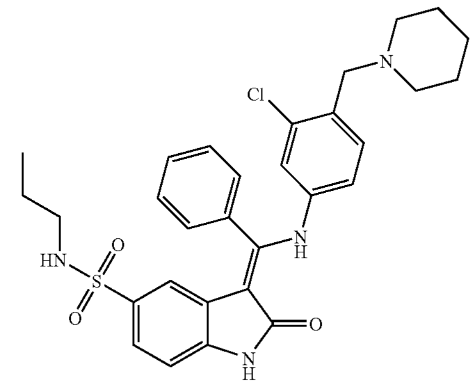 | 1.59 | 381 | 565.3 |
| 18 | 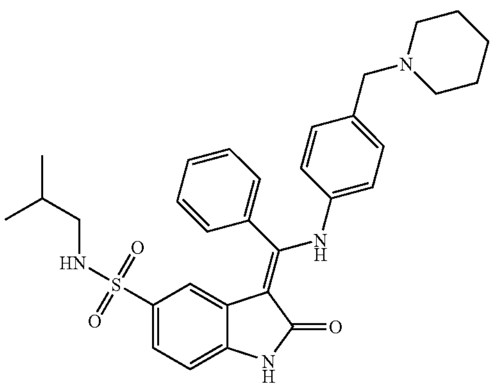 | 1.58 | 377 | 545.3 |
| 19 | 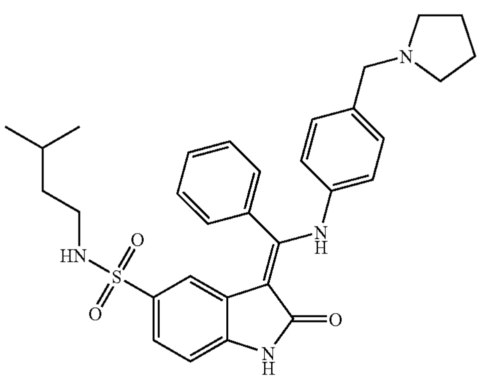 | 1.61 | 376 | 545.3 |
| 20 | 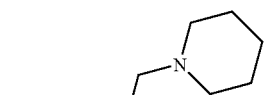 | 1.56 | 379 | 557.3 |

-continued
| # | structure | t_Ret [min] | UV_max [nm] | [M + H]+ |
|---|---|---|---|---|
| 21 | 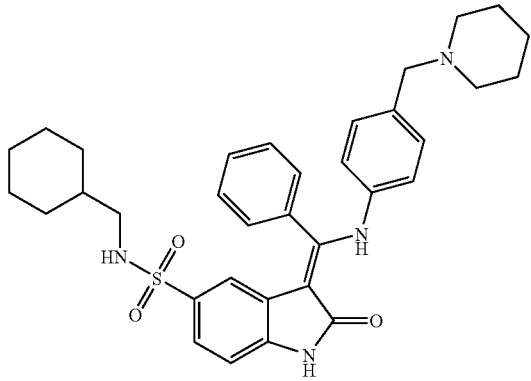 | 1.71 | 378 | 585.5 |
| 22 | 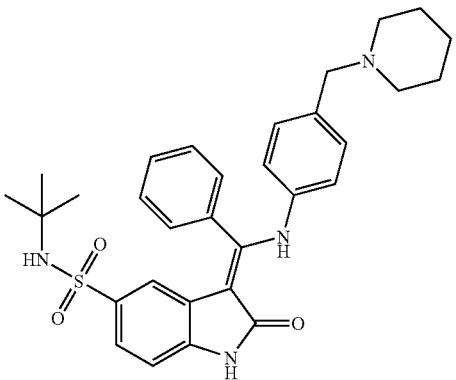 | 1.54 | 379 | 545.3 |
| 23 | 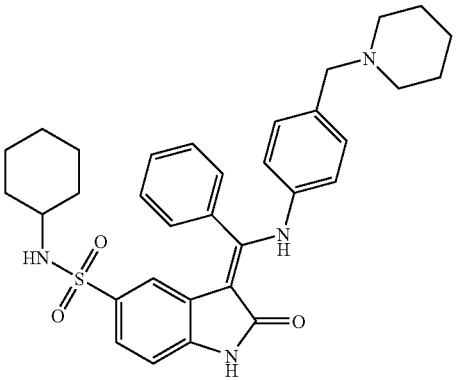 | 1.62 | 378 | 571.5 |
| 24 | 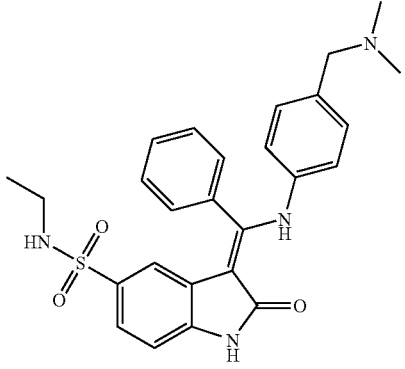 | 1.32 | 377 | 477.2 |

| # | structure | t_Ret [min] | UV_max [nm] | [M + H]+ |
|---|---|---|---|---|
| 25 | 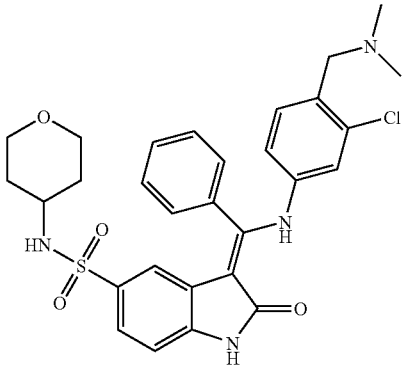 | 1.69 | 379 | 567.3 |
| 26 | 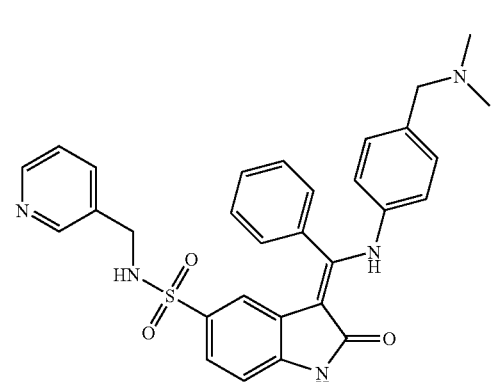 | 0.09 | 379 | 540.3 |
| 27 | 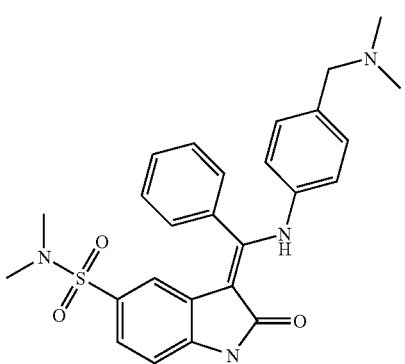 | 1.46 | 381 | 477.5 |
| 28 | 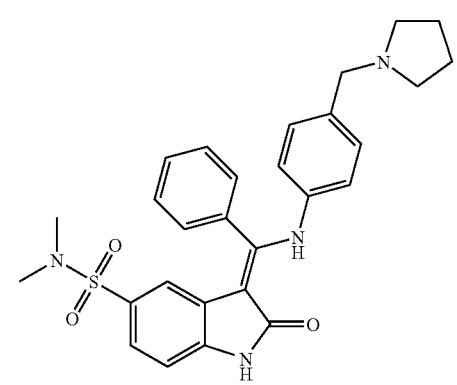 | 1.49 | 378 | 503.3 |

-continued

| # | structure | $t_{Ret}$ [min] | $UV_{max}$ [nm] | $[M + H]^+$ |
|---|---|---|---|---|
| 29 | 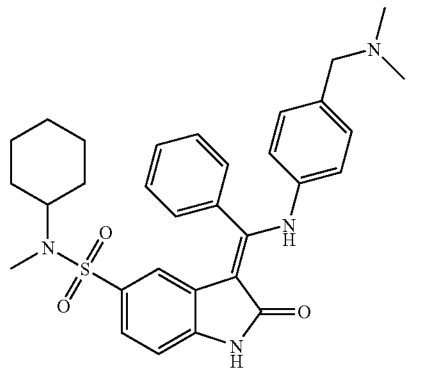 | 1.68 | 380 | 545.3 |
| 30 | 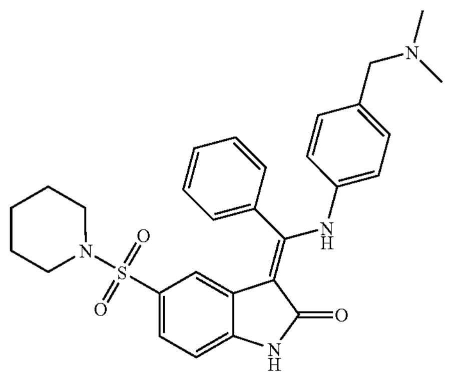 | 1.58 | 378 | 517.5 |
| 31 | 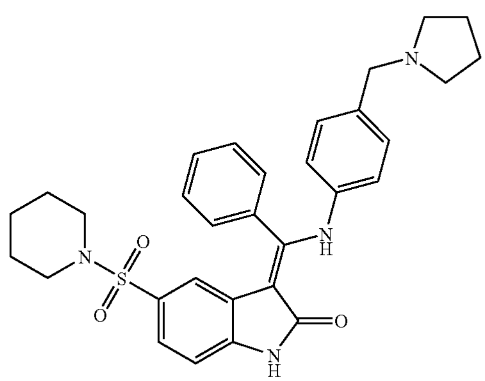 | 1.62 | 382 | 543.2 |
| 32 | 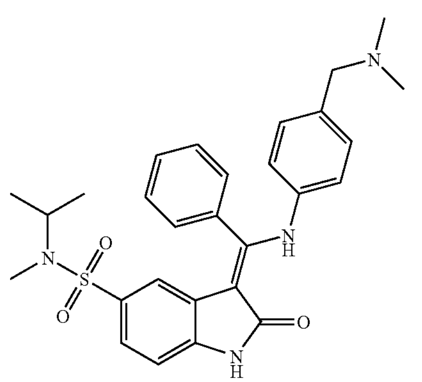 | 1.55 | 377 | 505.5 |

-continued
| # | structure | $t_{Ret}$ [min] | $UV_{max}$ [nm] | $[M+H]^+$ |
|---|---|---|---|---|
| 33 | 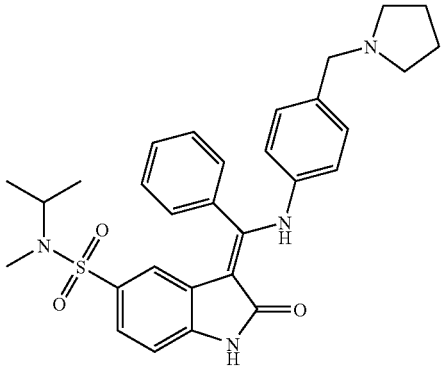 | 1.59 | 378 | 531.2 |
| 34 | 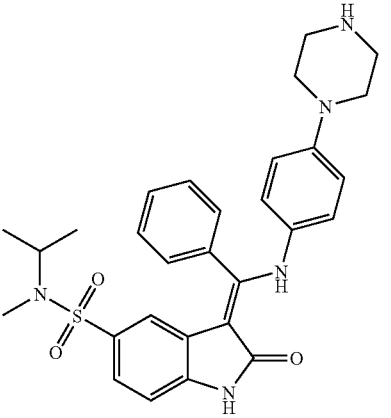 | 1.53 | 375 | 532.3 |
| 35 | 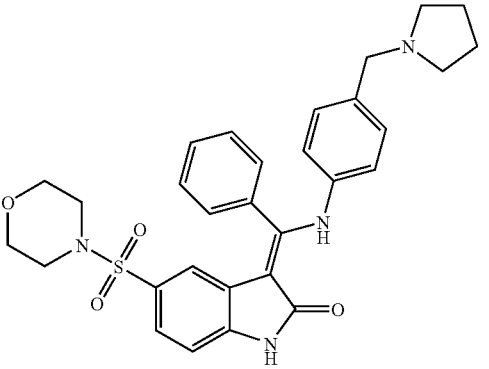 | 1.46 | 378 | 545.3 |

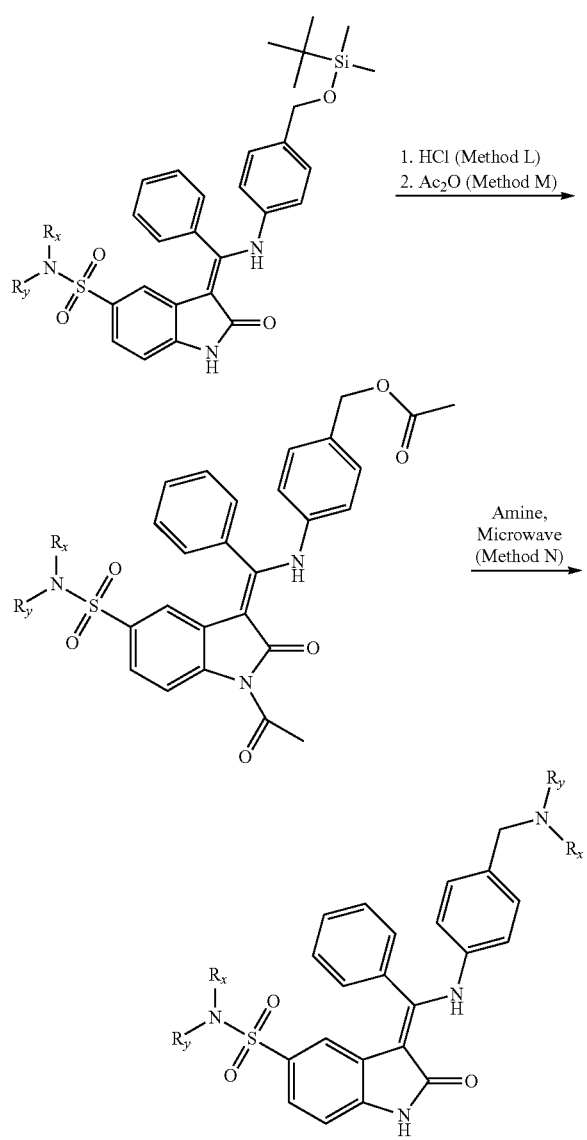

3-[1-[4-(tert-butyldimethylsilanyloxymethyl)phenylamino]-1-phenyl-meth-(Z)-ylidene]-2-oxo-2,3-dihydro-1H-indole-5-sulphonic acid cyclopropylmethylamide is prepared according to Method G using (4-tert-butyldimethylsilyloxymethyl)-aniline (Wendt et al., *J. Med. Chem.* 2004, 47, 303-324). The reaction solution is further reacted directly in THF.

Method L—3-[1-(4-hydroxymethylphenylamino)-1-phenyl-meth-(Z)-ylidene]-2-oxo-2,3-dihydro-1H-indole-5-sulphonic Acid Cyclopropylmethylamide 3-[1-[4-(tert-butyldimethylsilanyloxymethyl)phenylamino]-1-phenyl-meth-(Z)-ylidene]-2-oxo-2,3-dihydro-1H-indole-5-sulphonic acid cyclopropylmethylamide (3.7 g, 6.27 mmol) in THF (15 mL, reaction solution from the previous step) is combined with 6 N HCl (6 mL) and stirred for 3 h at RT. The reaction mixture is diluted with water (150 mL) and extracted exhaustively with EtOAc. The combined organic phases are washed with 0.1 N HCl, water, saturated potassium carbonate solution and saturated saline solution, dried on $Na_2SO_4$, filtered and evaporated down. Yield: 2.38 g Method M—4-[[[1-acetyl-5-(cyclopropylmethylsulphamoyl)-2-oxo-1,2-dihydro-indol-(3Z)-ylidene]phenylmethyl]amino]benzyl Acetate 3-[1-(4-hydroxymethylphenylamino)-1-phenyl-meth-(Z)-ylidene]-2-oxo-2,3-dihydro-1H-indole-5-sulphonic acid cyclopropylmethylamide (2.38 g, 5 mmol) and acetic anhydride (1.9 mL, 20.1 mmol) are stirred in anhydrous THF (10 mL) for 20 min at 125° C. in the microwave. The reaction mixture is diluted with dichloromethane (50 mL), washed with water and saturated saline solution, dried on $Na_2SO_4$, filtered and evaporated down.
Yield: 2.4 g Method N—2-oxo-3-[1-phenyl-1-(4-pyrrolidin-1-ylmethylphenyl-amino)meth-(Z)-ylidene]-2,3-dihydro-1H-indole-5-sulphonic Acid Cyclopropylmethylamide 4-[[[1-acetyl-5-(cyclopropylmethylsulphamoyl)-2-oxo-1,2-dihydro-indol-(3Z)-ylidene]phenylmethyl]amino]benzyl acetate (80 mg, 0.14 mmol) and pyrrolidine (118 μL, 1.43 mmol) are stirred in anhydrous NMP (500 μL) for 20 min at 180° C. in the microwave. The crude product is purified by preparative HPLC/MS and freeze-dried. Yield: 16 mg Thermally unstable amines are reacted at 160-170° C.

EXAMPLES 36-60

| Ex. | structure | $t_{Ret}$ [min] | $UV_{max}$ [nm] | $[M + H]^+$ |
|---|---|---|---|---|
| 36 | 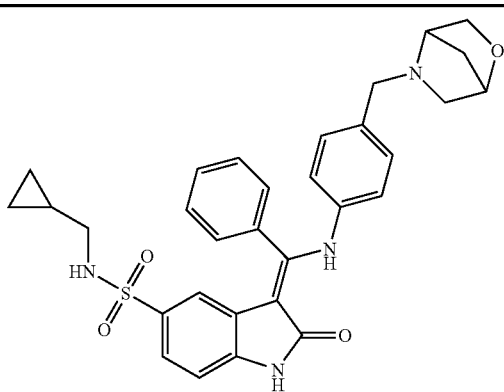 | 1.47 | 378 | 557.3 |

-continued
| Ex. | structure | $t_{Ret}$ [min] | $UV_{max}$ [nm] | $[M + H]^+$ |
|---|---|---|---|---|
| 37 | 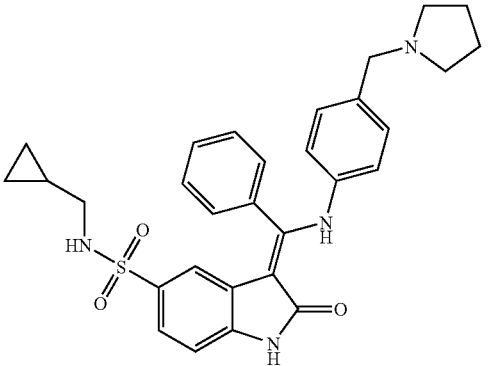 | 1.48 | 377 | 529.3 |
| 38 | 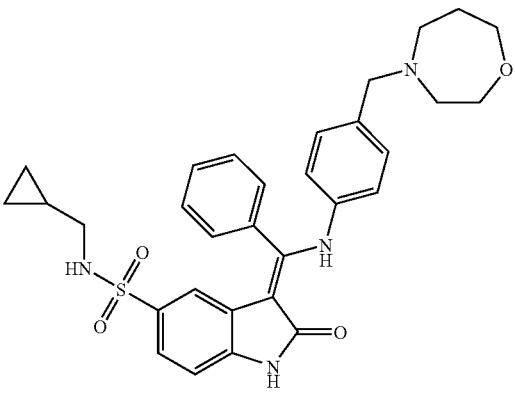 | 1.47 | 378 | 559.2 |
| 39 | 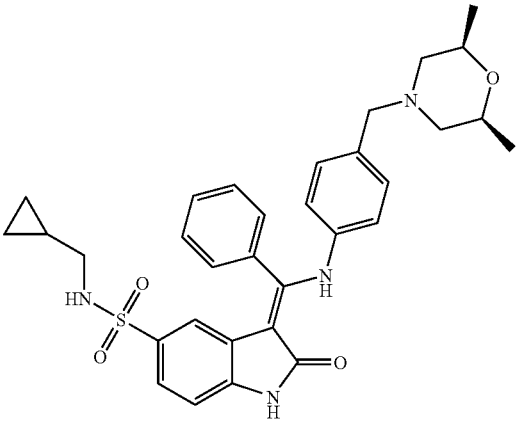 | 1.32 | 379 | 656.2 |
| 40 | 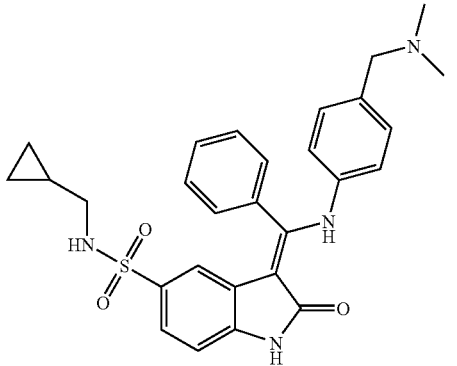 | 1.30 | 380 | 504.2 |

-continued
| Ex. | structure | $t_{Ret}$ [min] | $UV_{max}$ [nm] | $[M + H]^+$ |
|---|---|---|---|---|
| 41 | 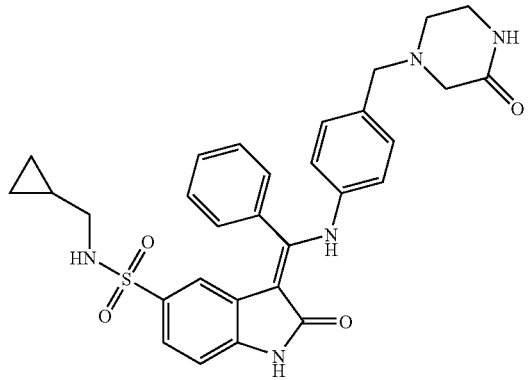 | 1.48 | 379 | 558.5 |
| 42 | 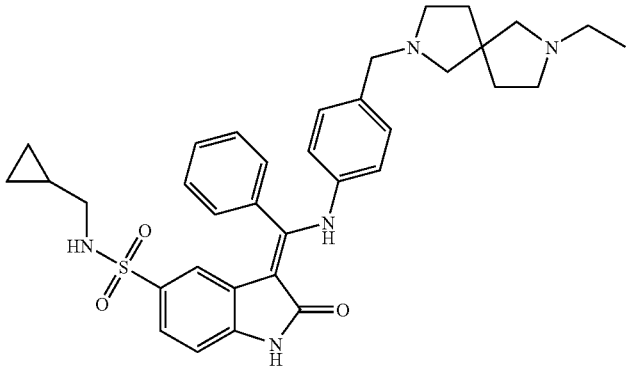 | 1.28 | 380 | 612.5 |
| 43 | 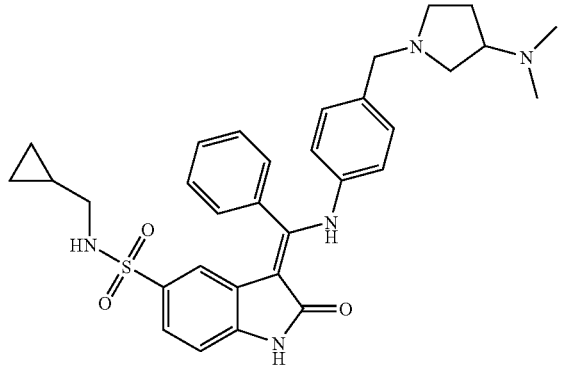 | 1.25 | 375 | 572.3 |
| 44 | 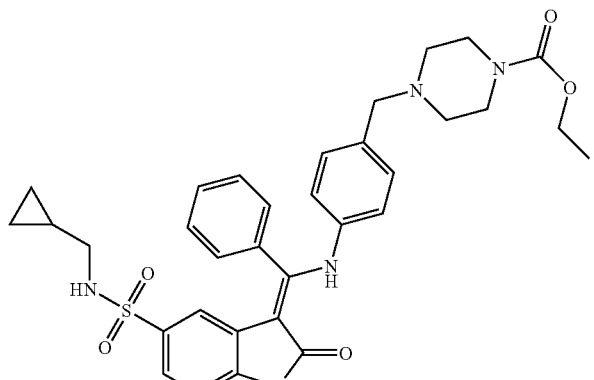 | 1.54 | 377 | 616.2 |

-continued

| Ex. | structure | t_Ret [min] | UV_max [nm] | [M + H]+ |
|---|---|---|---|---|
| 45 | 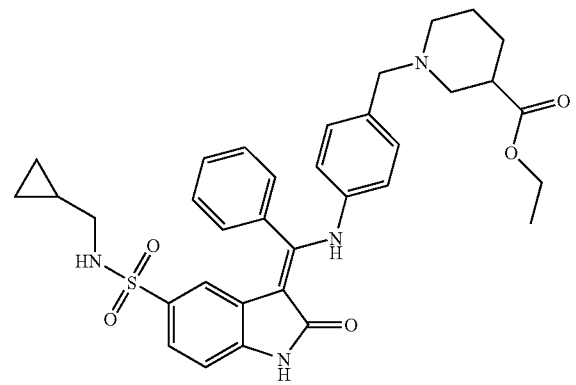 | 1.58 | 379 | 615.2 |
| 46 | 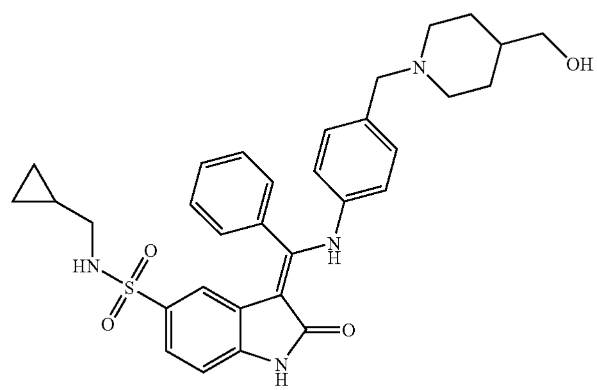 | 1.44 | 379 | 573.3 |
| 47 | 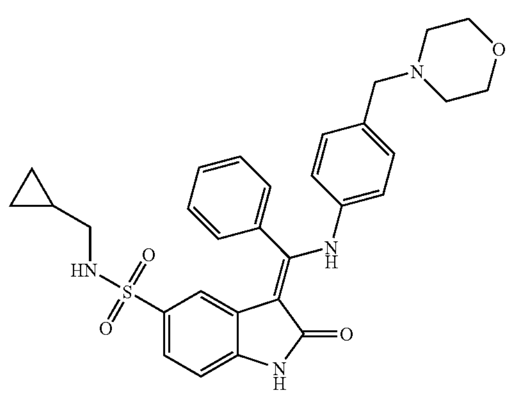 | 1.42 | 379 | 545.3 |
| 48 | 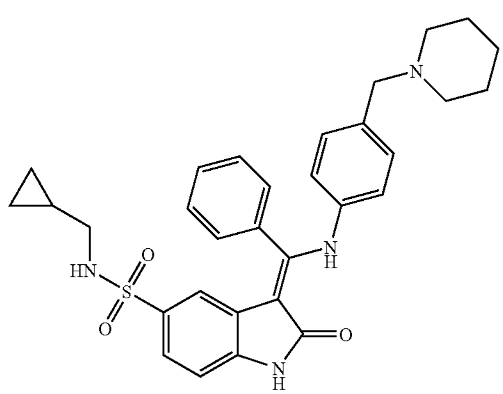 | 1.52 | 379 | 543.2 |

-continued

| Ex. | structure | $t_{Ret}$ [min] | $UV_{max}$ [nm] | $[M + H]^+$ |
|---|---|---|---|---|
| 49 | 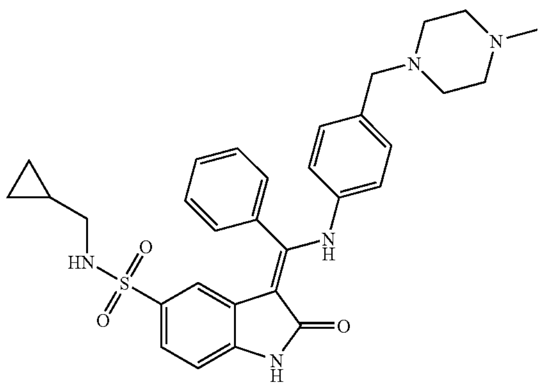 | 1.45 | 378 | 558.3 |
| 50 | 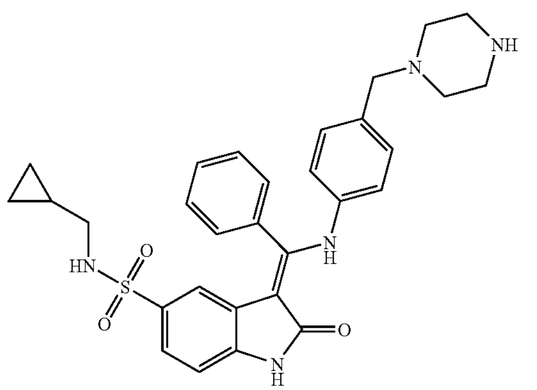 | 1.38 | 378 | 544.2 |
| 51 | 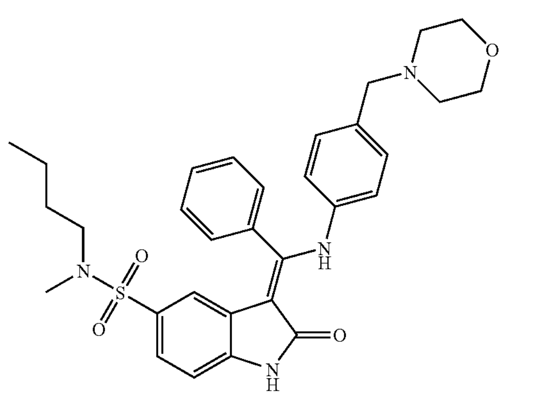 | 1.65 | 380 | 561.2 |
| 52 | 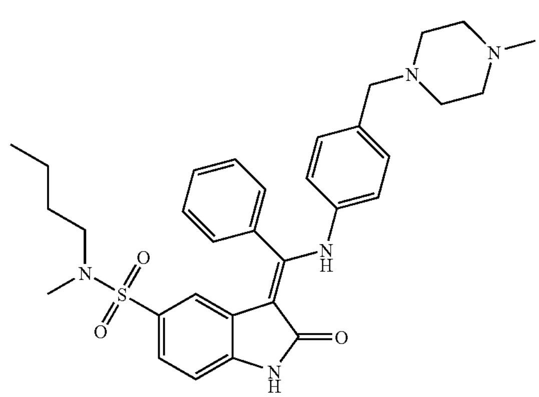 | 1.64 | 375 | 574.5 |

-continued

| Ex. | structure | $t_{Ret}$ [min] | $UV_{max}$ [nm] | $[M + H]^+$ |
|---|---|---|---|---|
| 53 | 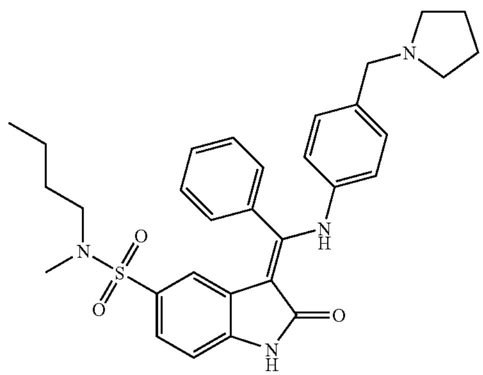 | 1.67 | 375 | 545.3 |
| 54 | 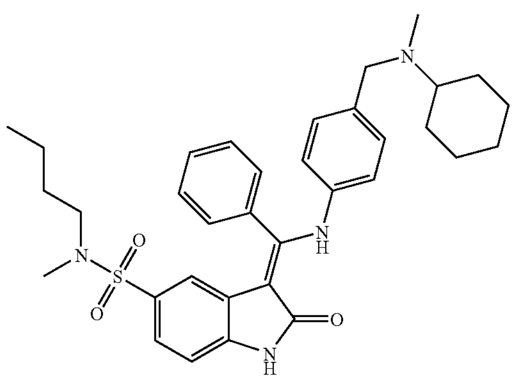 | 1.79 | 377 | 587.5 |
| 55 | 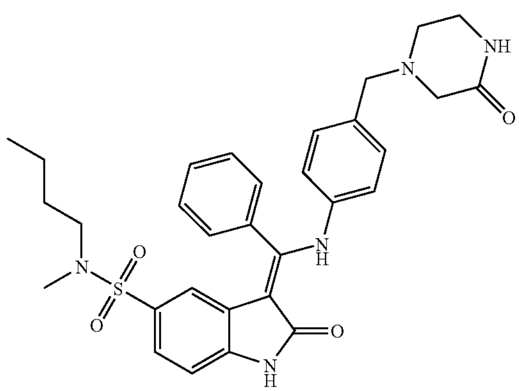 | 1.69 | 378 | 574.2 |
| 56 | 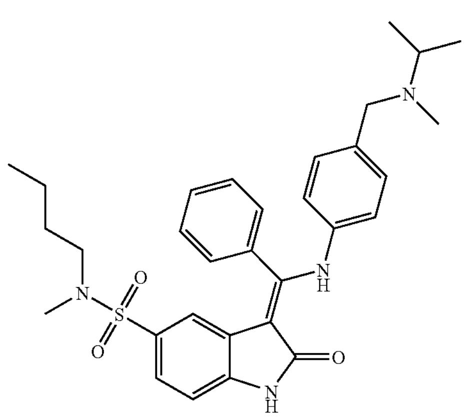 | 1.68 | 379 | 547.2 |

| Ex. | structure | $t_{Ret}$ [min] | $UV_{max}$ [nm] | [M + H]⁺ |
|---|---|---|---|---|
| 57 | 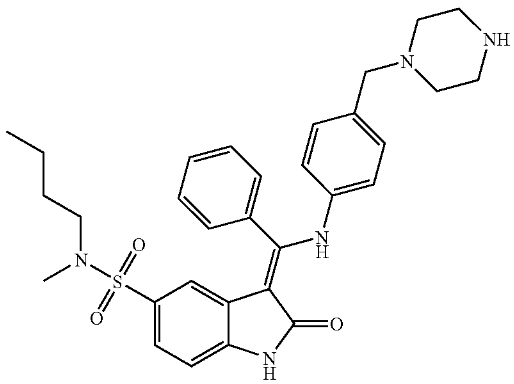 | 1.57 | 377 | 560.2 |
| 58 | 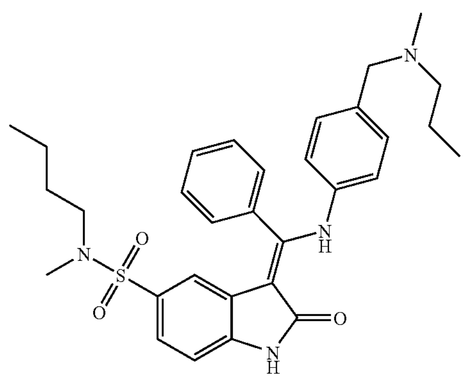 | 1.69 | 377 | 547.2 |
| 59 | 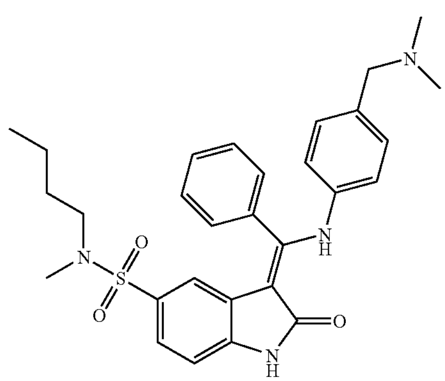 | 1.64 | 378 | 519.2 |
| 60 | 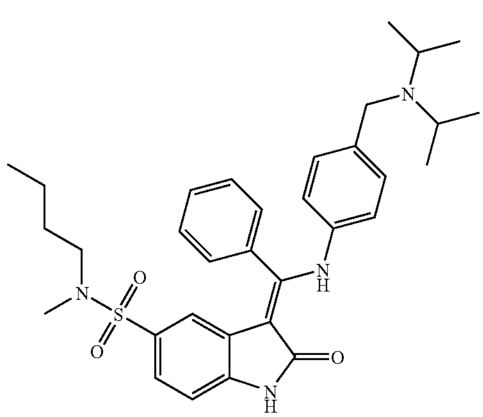 | 1.73 | 377 | 575.5 |

Method H—Preparation of 1-(1-methylpiperidin-4-yl)-4-(4-nitrophenyl)piperazine

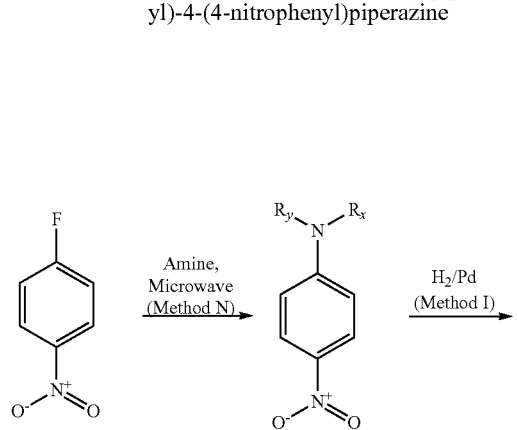

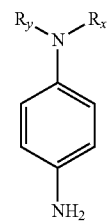

4-Fluoronitrobenzene (3 g, 21.3 mmol), 1-(1-methylpiperidin-4-yl)piperazine (3.9 g, 21.2 mmol) and triethylamine (3.30 mL, 23.7 mmol) are stirred in anhydrous isopropanol (10 mL) for 10 min at 160° C. in the microwave. The reaction mixture is diluted with water (10 mL), the precipitate is filtered off washed with 50% water in isopropanol and dried in vacuo at 45° C. Yield: 5.14 g If no crystalline product is obtained the crude mixture is evaporated down, worked up by extraction and optionally purified by chromatography.

| # | structure | educt |
|---|---|---|
| H.1 | 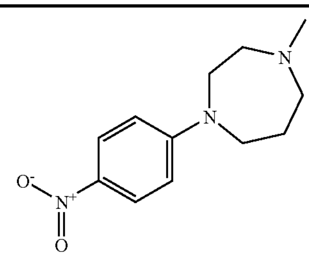 | |
| H.2 | 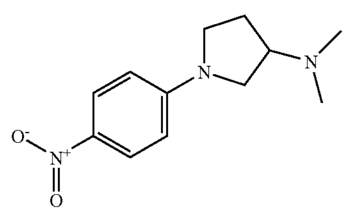 | |
| H.3 | 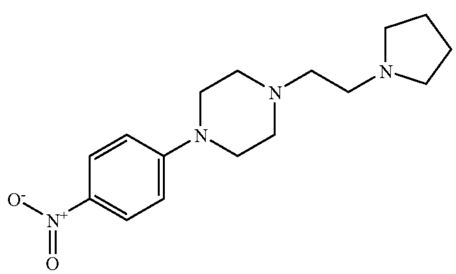 | |

Method I—4-[4-(1-methylpiperidin-4-yl)piperazin-1-yl]phenylamine 1-(1-methylpiperidin-4-yl)-4-(4-nitrophenyl)piperazine (5.14 g, 16.8 mmol) is dissolved in anhydrous THF (10 mL), combined with 10% palladium on activated charcoal and hydrogenated for 17 h at 3 bar hydrogen pressure at RT. Additional catalyst is optionally metered in and the hydrogen pressure is readjusted as it falls. The reaction mixture is filtered, evaporated down, combined with toluene (3×200 mL) and evaporated down again. Yield: 4.52 g

| # | structure | educt |
|---|---|---|
| I.1 | 4-(4-methyl-1,4-diazepan-1-yl)aniline | 1-methyl-4-(4-nitrophenyl)-1,4-diazepane |
| I.2 | 4-[3-(dimethylamino)pyrrolidin-1-yl]aniline | N,N-dimethyl-1-(4-nitrophenyl)pyrrolidin-3-amine |
| I.3 | 4-{4-[2-(pyrrolidin-1-yl)ethyl]piperazin-1-yl}aniline | 1-[2-(4-(4-nitrophenyl)piperazin-1-yl)ethyl]pyrrolidine |

3-[1-(4-aminophenylamino)-1-phenylmeth-(Z)-ylidene]-2-oxo-2,3-dihydro-1H-indole-5-sulphonamide derivatives are prepared according to Method G.

EXAMPLES 61-85

| Ex. | structure | $t_{Ret}$ [min] | $UV_{max}$ [nm] | $[M + H]^+$ |
|---|---|---|---|---|
| 61 | (structure) | 1.49 | 381 | 558.3 |

-continued
| Ex. | structure | $t_{Ret}$ [min] | $UV_{max}$ [nm] | $[M + H]^+$ |
|---|---|---|---|---|
| 62 | 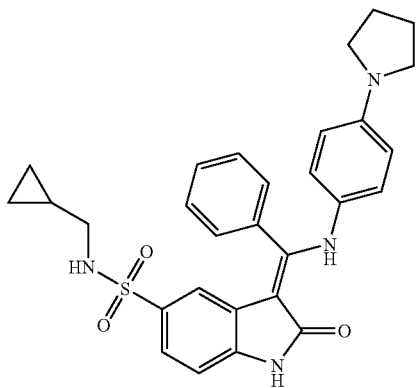 | 2.22 | 389 | 515.2 |
| 63 | 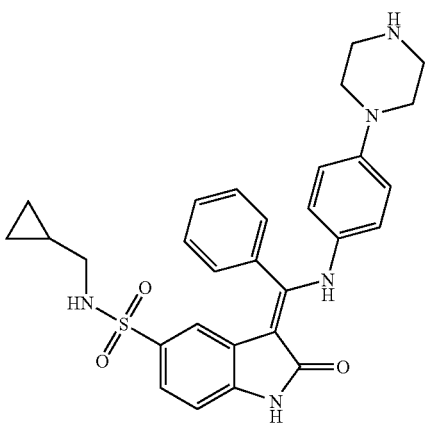 | 1.45 | 381 | 530.2 |
| 64 | 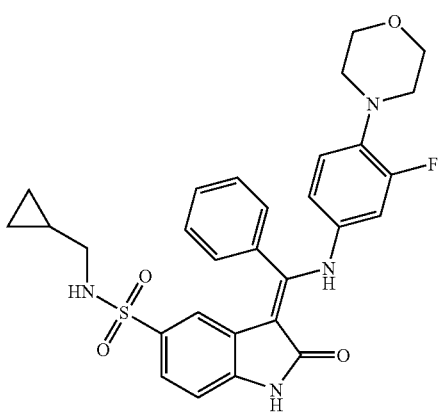 | 2.03 | 383 | 549.3 |

-continued
| Ex. | structure | t_Ret [min] | UV_max [nm] | [M + H]+ |
|---|---|---|---|---|
| 65 | 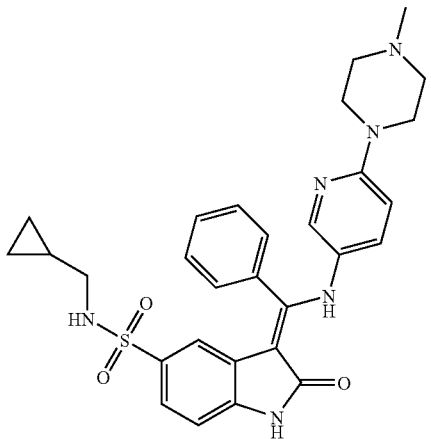 | 1.42 | 370 | 545.3 |
| 66 | 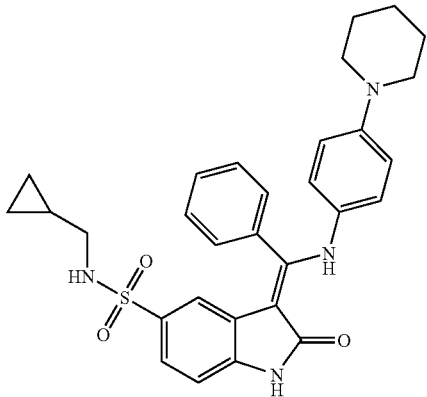 | 1.79 | 378 | 529.3 |
| 67 | 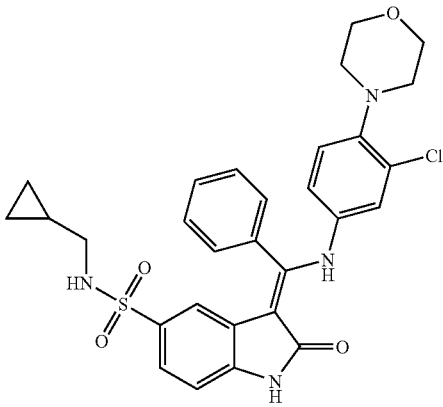 | 2.11 | 380 | 565.3 |

-continued
| Ex. | structure | t_Ret [min] | UV_max [nm] | [M + H]+ |
|---|---|---|---|---|
| 68 | 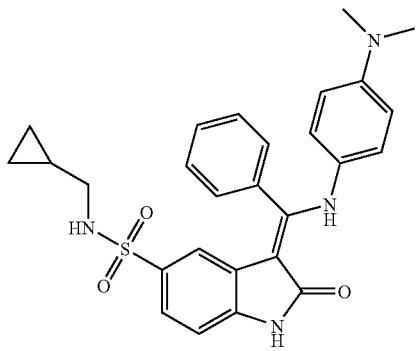 | 1.91 | 372 | 489.2 |
| 69 | 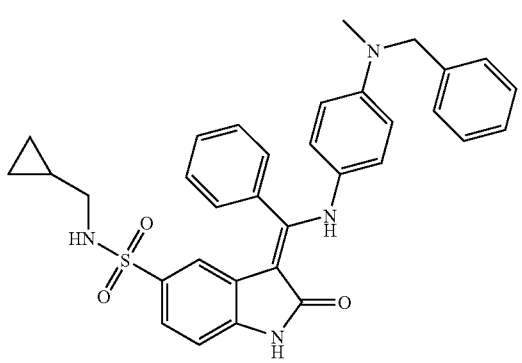 | 2.29 | 386 | 565.3 |
| 70 | 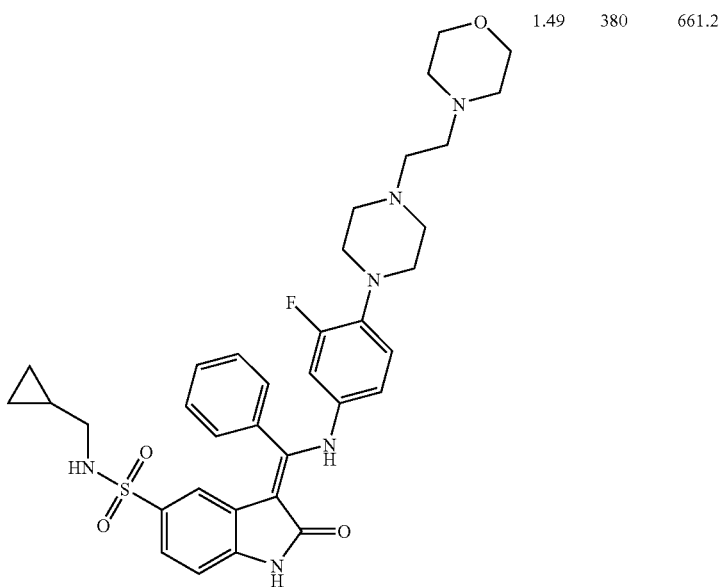 | 1.49 | 380 | 661.2 |

-continued

| Ex. | structure | t_Ret [min] | UV_max [nm] | [M + H]+ |
|---|---|---|---|---|
| 71 | 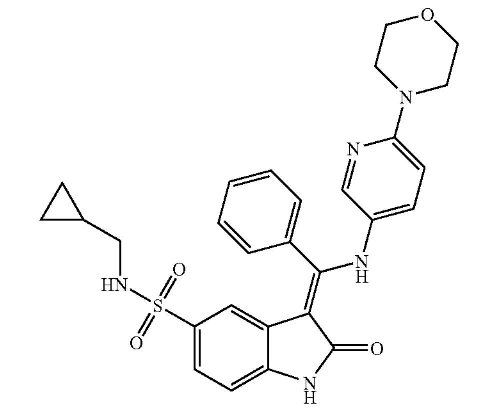 | 1.79 | 373 | 532.3 |
| 72 | 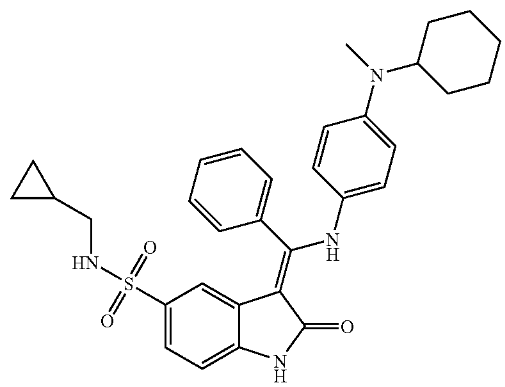 | 1.98 | 378 | 557.3 |
| 73 | 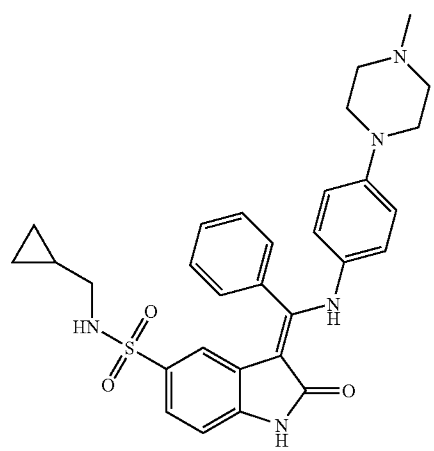 | 1.48 | 381 | 544.5 |
| 74 | 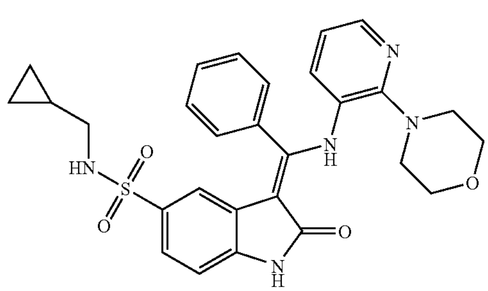 | 1.89 | 389 | 532.3 |

-continued

| Ex. | structure | t_Ret [min] | UV_max [nm] | [M + H]+ |
|---|---|---|---|---|
| 75 | 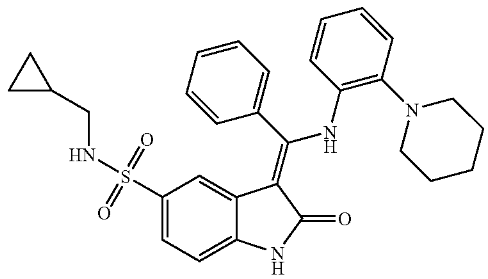 | 2.33 | 391 | 529.3 |
| 76 | 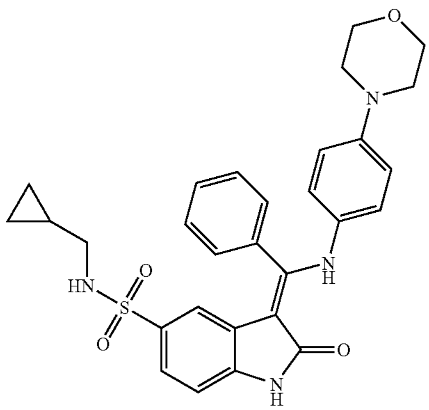 | 1.96 | 383 | 531.2 |
| 77 | 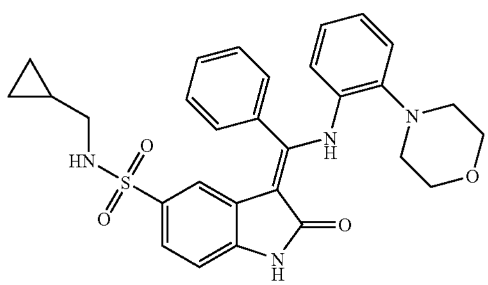 | 2.08 | 388 | 531.2 |
| 78 | 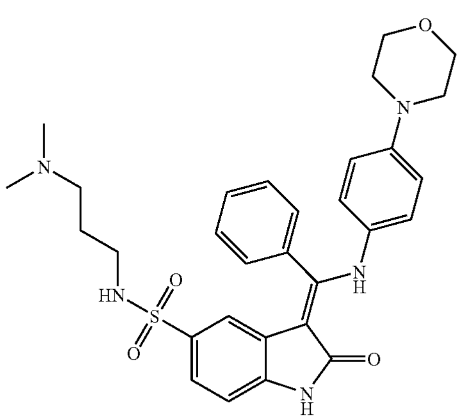 | 1.52 | 379 | 562.3 |

-continued
| Ex. | structure | $t_{Ret}$ [min] | $UV_{max}$ [nm] | $[M + H]^+$ |
|---|---|---|---|---|
| 79 | 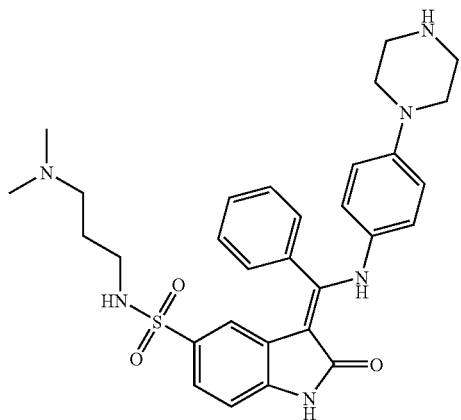 | 0.12 | 388 | 561.3 |
| 80 | 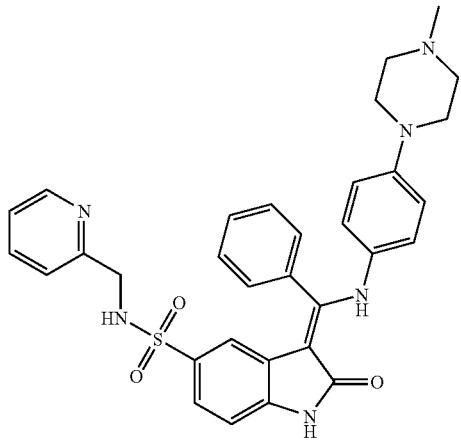 | 1.27 | 381 | 581.3 |
| 81 | 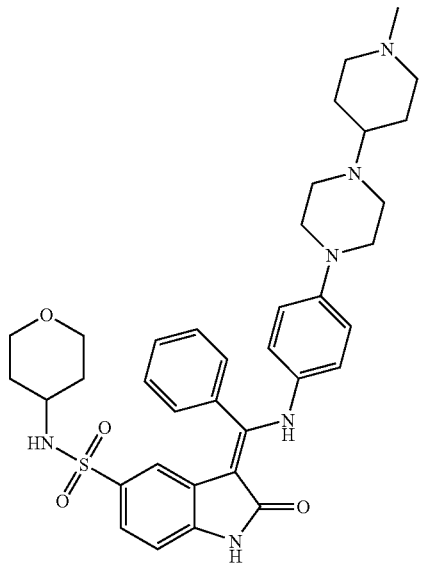 | 0.17 | 379 | 657.3 |

-continued
| Ex. | structure | t_Ret [min] | UV_max [nm] | [M + H]+ |
|---|---|---|---|---|
| 82 | 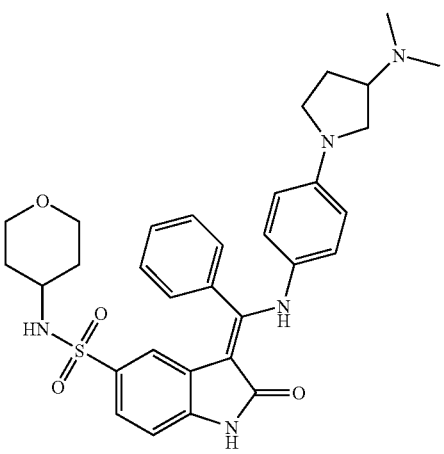 | 1.66 | 384 | 588.3 |
| 83 | 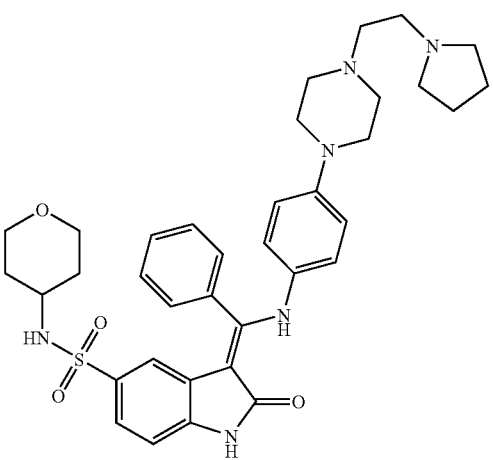 | 1.54 | 378 | 657.3 |
| 84 | 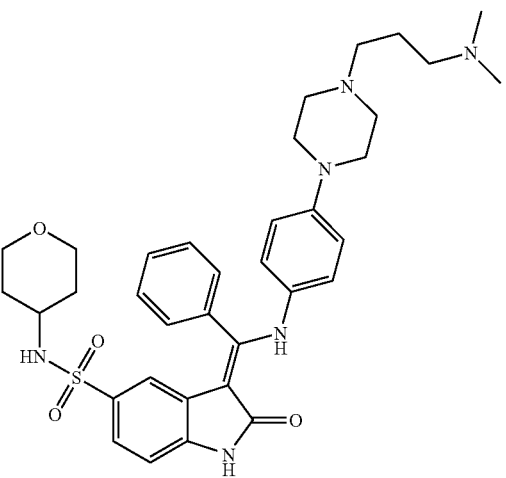 | 0.16 | 380 | 645.3 |

| Ex. | structure | t$_{Ret}$ [min] | UV$_{max}$ [nm] | [M + H]$^+$ |
|---|---|---|---|---|
| 85 | 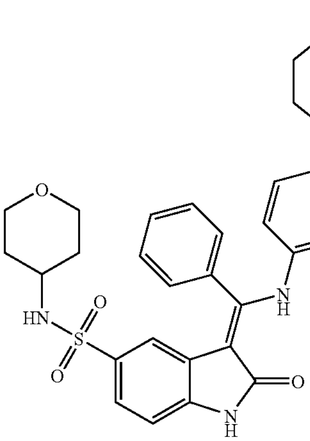 | 1.65 | 386 | 588.3 |

Derivatives with a modification to the left-hand phenyl nucleus are prepared in a manner which is highly analogous to the corresponding phenyl compounds.

EXAMPLES 86-94

| Ex. | structure | t$_{Ret}$ [min] | UV$_{max}$ [nm] | [M + H]$^+$ |
|---|---|---|---|---|
| 86 | 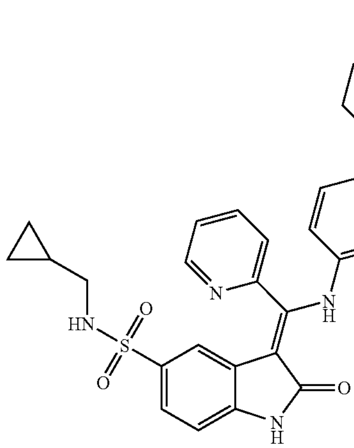 | 1.33 | 381 | 545.3 |
| 87 | 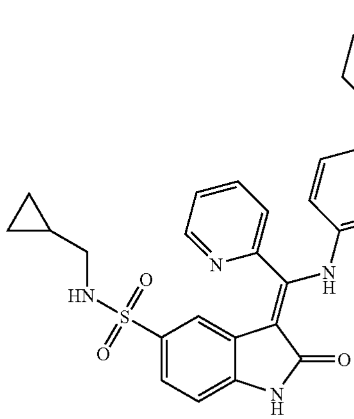 | 0.65 | 388 | 532.3 |

| Ex. | structure | $t_{Ret}$ [min] | $UV_{max}$ [nm] | $[M + H]^+$ |
|---|---|---|---|---|
| 88 | 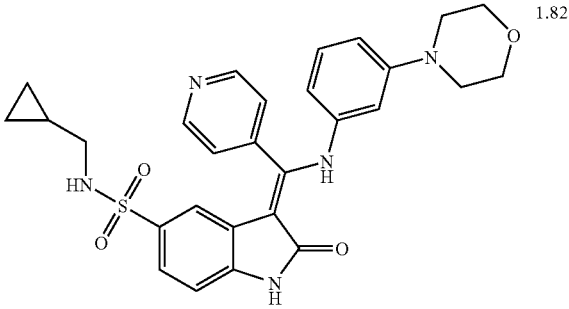 | 1.82 | 390 | 532.3 |
| 89 | 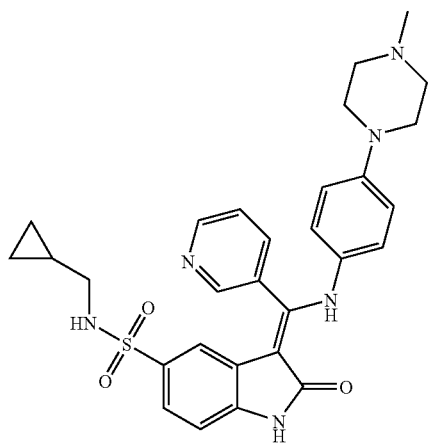 | 1.31 | 382 | 545.3 |
| 90 | 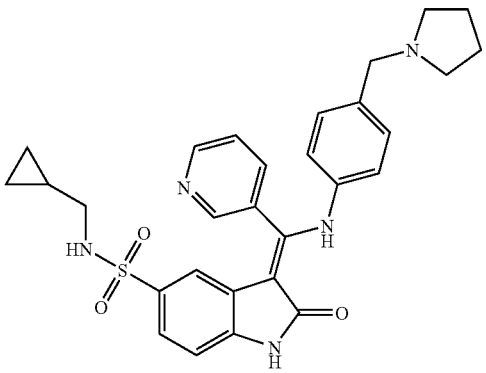 | 1.27 | 382 | 530.2 |
| 91 | 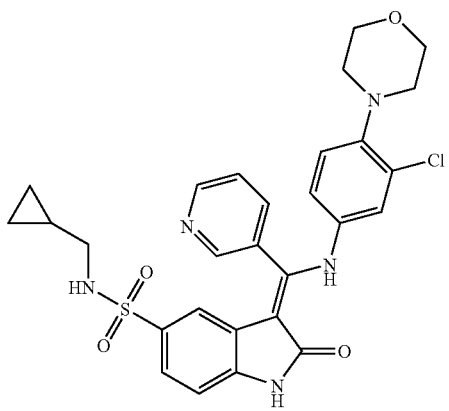 | 1.90 | 380 | 566.2 |

-continued
| Ex. | structure | $t_{Ret}$ [min] | $UV_{max}$ [nm] | $[M + H]^+$ |
|---|---|---|---|---|
| 92 | 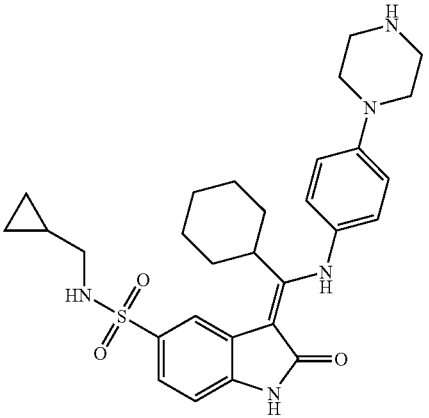 | 1.55 | 355 | 536.2 |
| 93 | 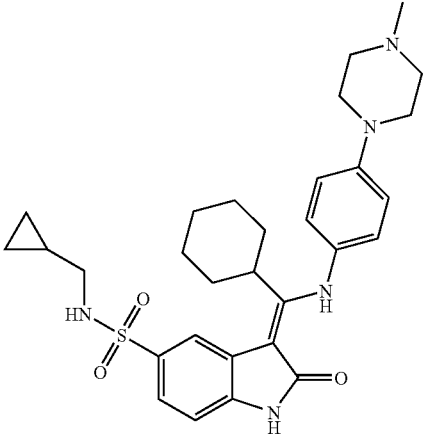 | 1.55 | 356 | 550.2 |
| 94 | 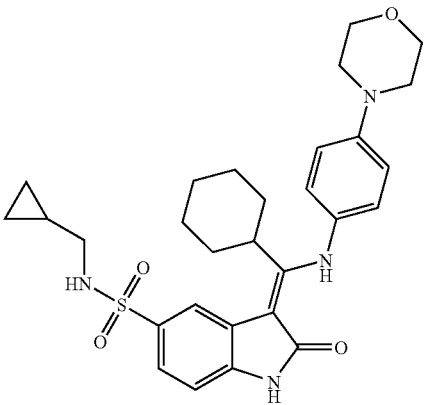 | 2.11 | 355 | 537.3 |

Method O—2-oxo-3-[1-phenyl-1-(4-pyrrolidin-1-ylmethylphenyl-amino)meth-(Z)-ylidene]-2,3-dihydro-1H-indole-5-sulphonic Acid piperidin-4-ylamide

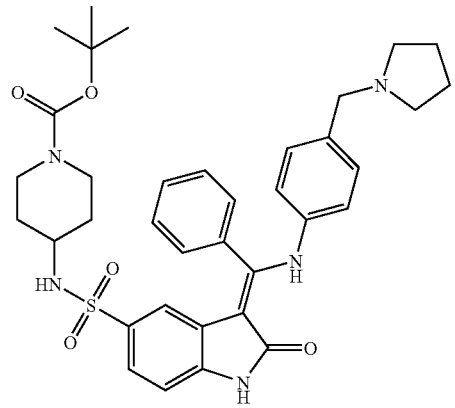

TFA
(Method O)

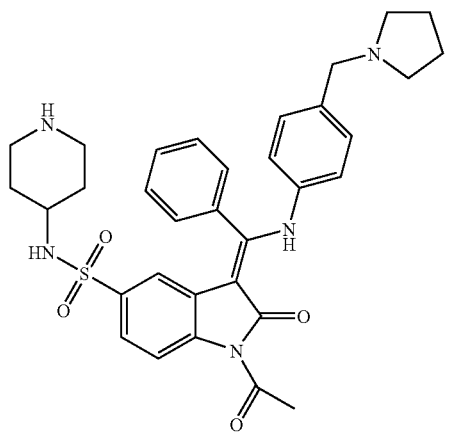

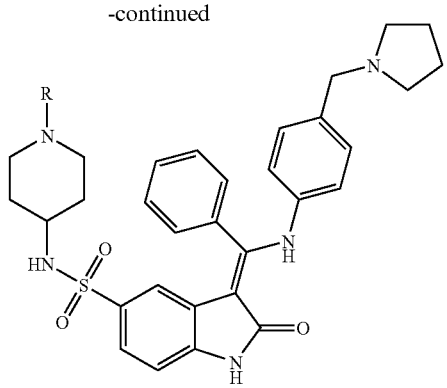

R = Acyl: R'COCl, Et₃N (Method P)
R = Alkylsulfonyl: R'SO₂Cl, Et₃N (Method Q)
R = Alkyl: RHal, K₂CO₃ (Method R)

tert-Butyl 4-[2-oxo-3-[1-phenyl-1-(4-pyrrolidin-1-ylmethylphenylamino)-meth-(Z)-ylidene]-2,3-dihydro-1H-indole-5-sulphonylamino]-piperidine-1-carboxylate (240 mg, 0.36 mmol) is stirred for 2 h in 50% trifluoroacetic acid in dichloromethane. The reaction mixture is evaporated down and the residue is purified by column chromatography.
Yield: 203 mg

Method P—2-oxo-3-[1-phenyl-1-(4-pyrrolidin-1-ylmethylphenyl-amino)meth-(Z)-ylidene]-2,3-dihydro-1H-indole-5-sulphonic acid-(1-acetyl-piperidin-4-yl)amide 2-Oxo-3-[1-phenyl-1-(4-pyrrolidin-1-ylmethylphenylamino)meth-(Z)-ylidene]-2,3-dihydro-1H-indole-5-sulphonic acid piperidin-4-ylamide (130 mg, 0.12 mmol) is combined in anhydrous NMP with triethylamine (48 µL, 0.35 mmol) and acetyl chloride (10 µL, 1.2 mmol) and the mixture is stirred for 12 h at RT. The reaction mixture is purified by preparative HPLC/MS and freeze-dried. Yield: 40 mg

Method Q—2-oxo-3-[1-phenyl-1-(4-pyrrolidin-1-ylmethylphenyl-amino)meth-(Z)-ylidene]-2,3-dihydro-1H-indole-5-sulphonic acid-(1-methanesulphonylpiperidin-4-yl)amide This is prepared analogously to Method P using methanesulphonic acid chloride. Pyridine is optionally used instead of triethylamine as base.

EXAMPLES 95-100

| Ex. | structure | $t_{Ret}$ [min] | $UV_{max}$ [nm] | $[M + H]^+$ |
|---|---|---|---|---|
| 95 | 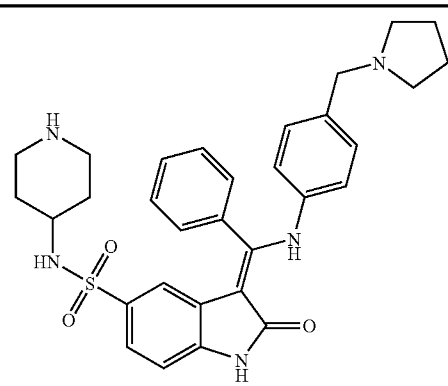 | 1.34 | 378 | 558.3 |

-continued

| Ex. | structure | t_Ret [min] | UV_max [nm] | [M + H]+ |
|---|---|---|---|---|
| 96 | 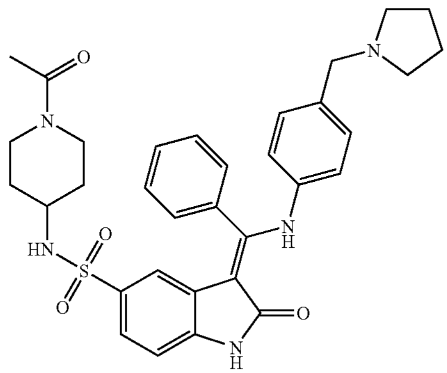 | 1.38 | 376 | 600.5 |
| 97 | 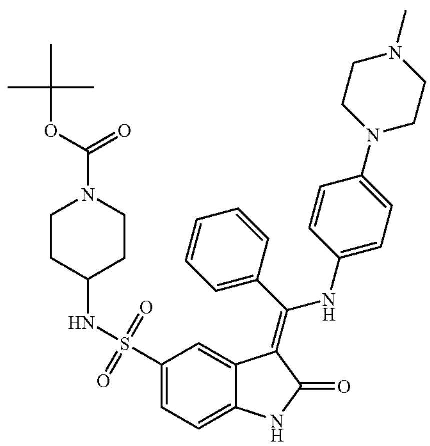 | 1.62 | 379 | 673.3 |
| 98 | 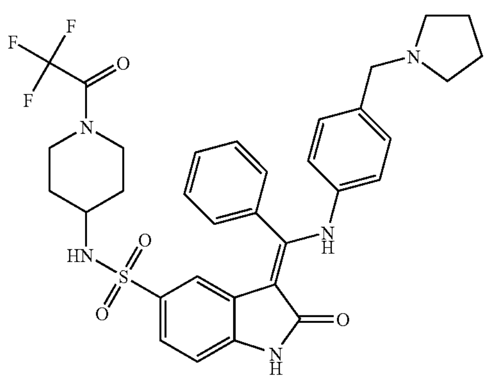 | 1.55 | 378 | 654.3 |
| 99 | 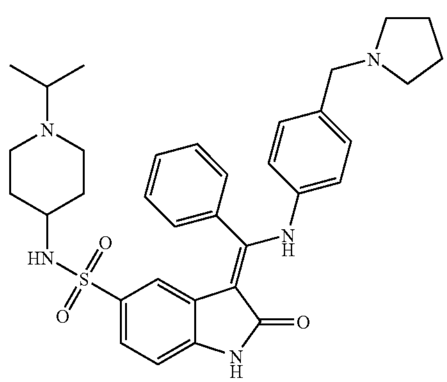 | 1.20 | 379 | 600.2 |

| Ex. | structure | $t_{Ret}$ [min] | $UV_{max}$ [nm] | $[M + H]^+$ |
|---|---|---|---|---|
| 100 | 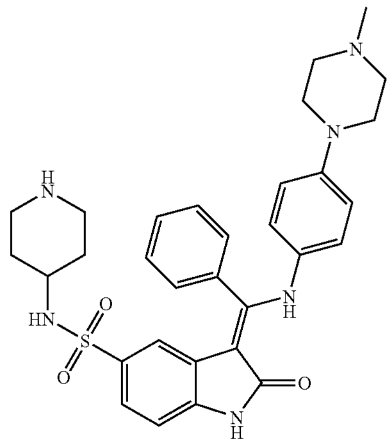 | 0.12 | 375 | 573.3 |

Methyl 4-[[[5-(N-butyl-N-methylsulphamoyl)-2-oxo-1,2-dihydroindol-(3Z)-ylidene]-phenylmethyl]amino]benzoate is prepared according to Method F.

Yield: 150 mg

Method U—4-[[[5-(N-butyl-N-methylsulphamoyl)-2-oxo-1,2-dihydroindol-(3Z)-ylidene]-phenylmethyl]amino]benzoic Acid

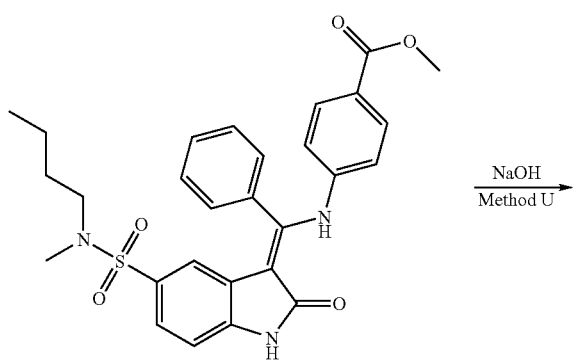

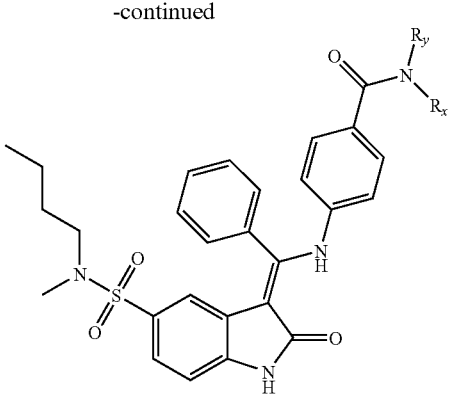

10 N NaOH (250 µL) is added to a solution of methyl 4-[[[5-(N-butyl-N-methylsulphamoyl)-2-oxo-1,2-dihydroindol-(3Z)-ylidene]-phenylmethyl]amino]benzoate (971 mg, 1.87 mmol) in methanol (5 mL) and the mixture is stirred for 30 min at RT. It is acidified with 1 N HCl, diluted with water (10 mL) and extracted exhaustively with EtOAc. The combined organic phases are washed with water and saturated saline solution, dried on $Na_2SO_4$, filtered and evaporated down. Yield: 600 mg Method V—2-oxo-3-[1-phenyl-1-[4-(pyrrolidin-1-carbonyl)phenylamino]-meth-(Z)-ylidene]-2,3-dihydro-1H-indole-5-sulphonic Acid-N-butyl-N-methylamide 4-[[[5-(N-butyl-N-methylsulphamoyl)-2-oxo-1,2-dihydroindol-(3Z)-ylidene]-phenylmethyl]amino]benzoic acid (50 mg, 0.10 mmol) in anhydrous NMP (500 µL) is combined with TBTU (47.7 mg, 0.15 mmol) and the mixture is stirred for 15 min at RT. Pyrrolidine (16 µL, 0.20 mmol) and N-ethyldiisopropylamine (59 µL, 0.15 mmol) are added and the mixture is stirred for 1 h at RT. The crude product is neutralised with formic acid, purified by preparative HPLC/MS and freeze-dried. Yield: 16 mg

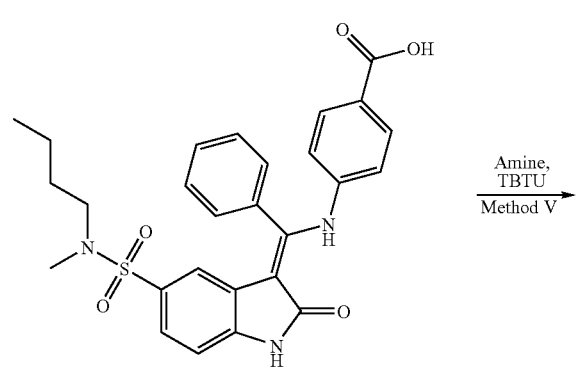

EXAMPLES 101-111
| Ex. | structure | $t_{Ret}$ [min] | $UV_{max}$ [nm] | $[M + H]^+$ |
|---|---|---|---|---|
| 101 | 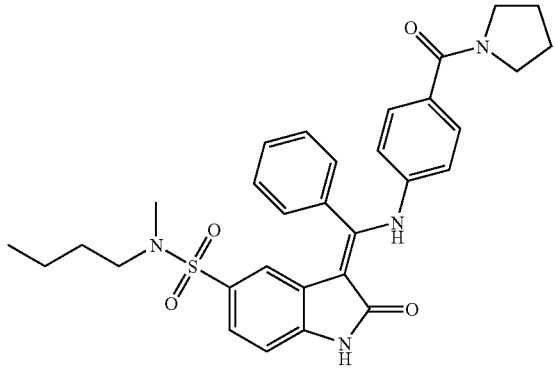 | 2.11 | 382 | 559.5 |
| 102 | 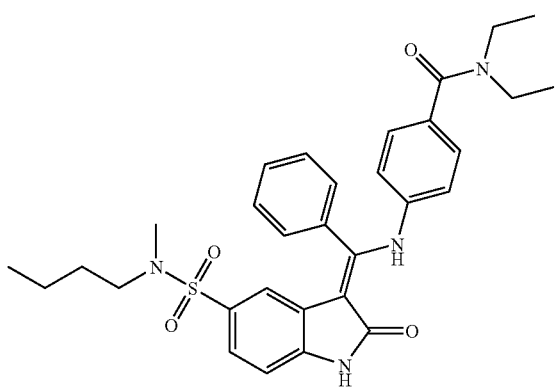 | 2.18 | 380 | 561.5 |
| 103 | 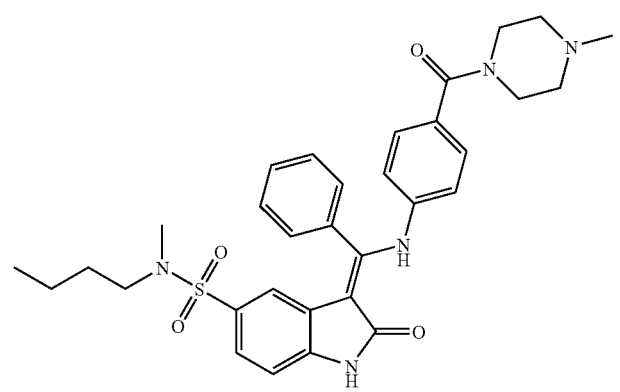 | 1.63 | 382 | 588.5 |
| 104 | 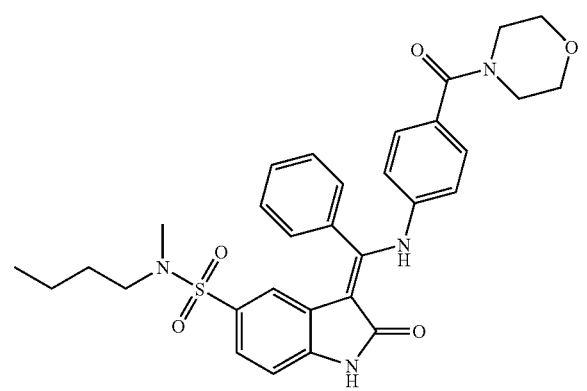 | 2.02 | 381 | 575.5 |

| Ex. | structure | t_Ret [min] | UV_max [nm] | [M + H]+ |
|---|---|---|---|---|
| 105 | 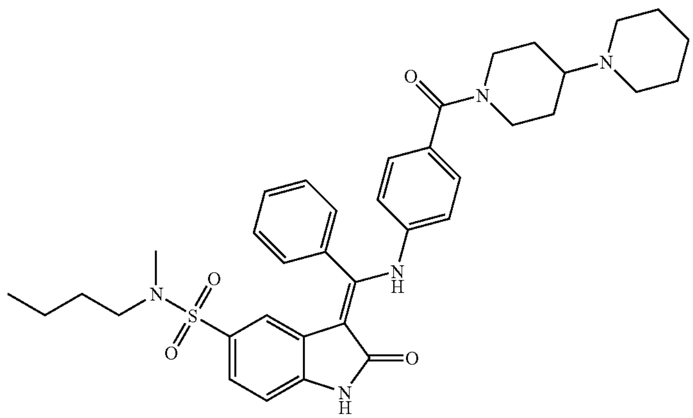 | 1.68 | 380 | 656.5 |
| 106 | 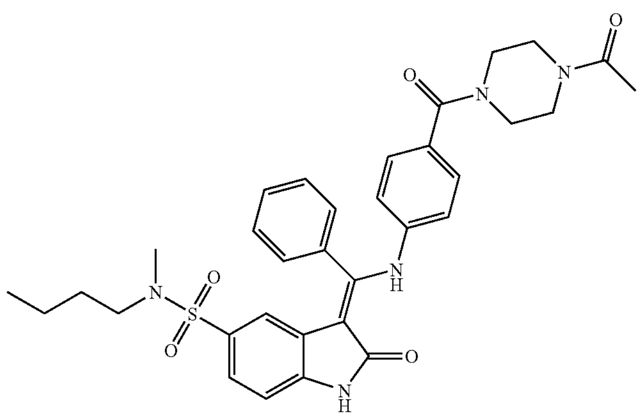 | 1.94 | 382 | 616.5 |
| 107 | 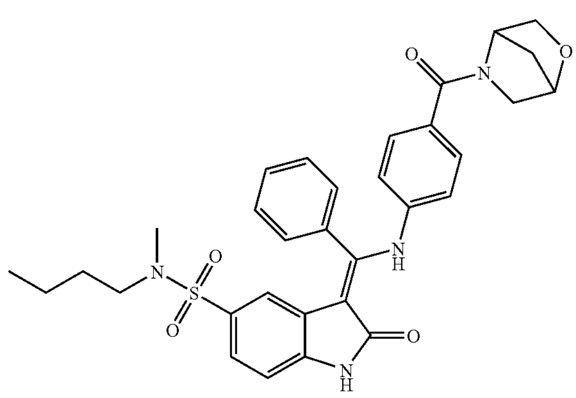 | 1.99 | 383 | 587.3 |

-continued
| Ex. | structure | $t_{Ret}$ [min] | $UV_{max}$ [nm] | $[M + H]^+$ |
|---|---|---|---|---|
| 108 | 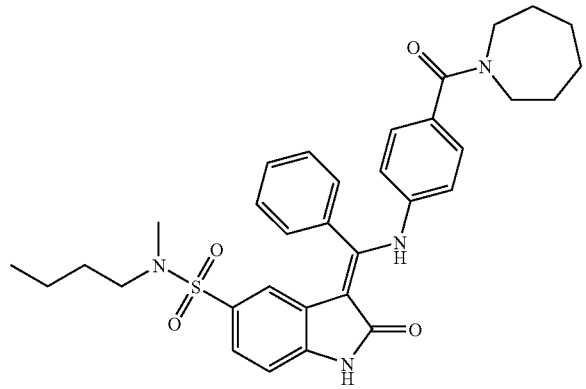 | 2.56 | 380 | 587.5 |
| 109 | 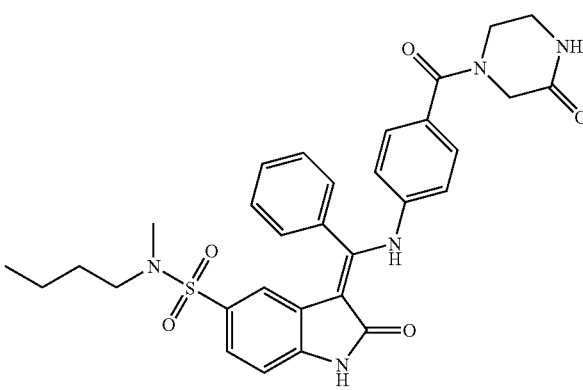 | 1.88 | 382 | 588.3 |
| 110 | 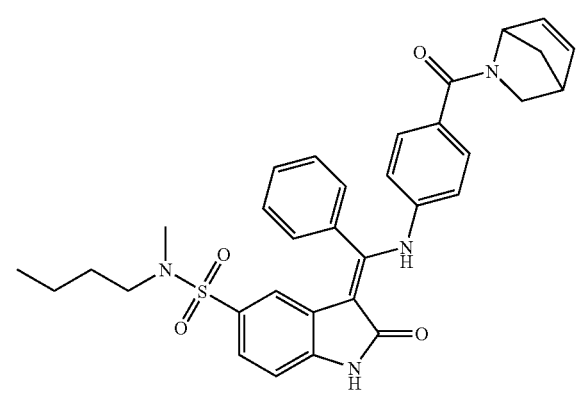 | 2.00 | 386 | 583.3 |
| 111 | 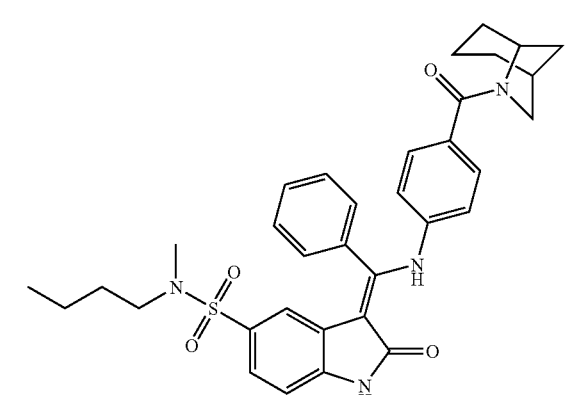 | 2.25 | 381 | 599.5 |

Method W—isobutyl 2-oxo-2,3-dihydro-1H-indole-5-sulphonate

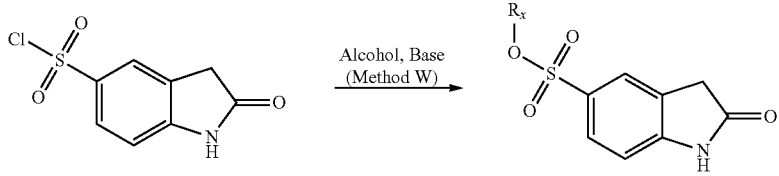

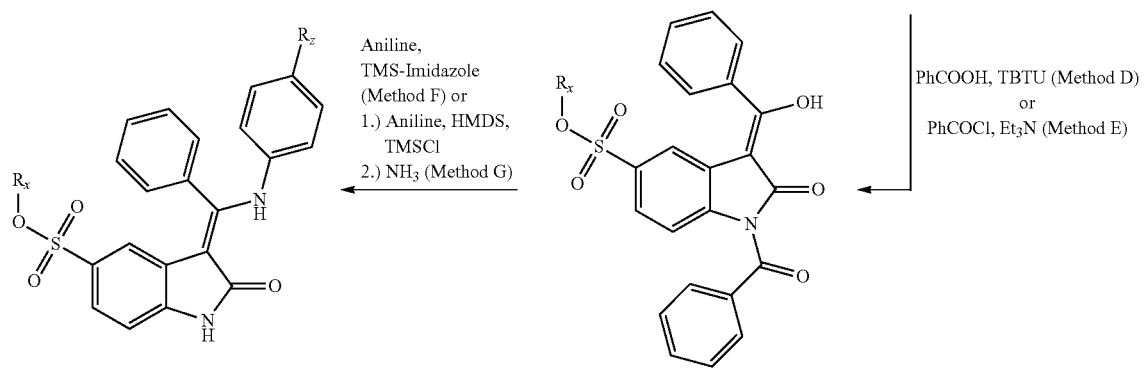

Pyridine (6 mL) is added dropwise within 5 min at 0° C. to a mixture of 2-oxo-2,3-dihydro-1H-indole-5-sulphonyl chloride (2 g, 8.63 mmol) and 2-methyl-1-propanol (6 mL) and the mixture is stirred for 1.5 h at RT. The reaction mixture is evaporated down, dissolved in dichloromethane, washed with 0.1 N HCl, water and saturated saline solution, dried on $Na_2SO_4$, filtered and evaporated down. The crude product may optionally be purified by chromatography. Yield: 2 g

| # | structure | educt |
|---|-----------|-------|
| W.1 | ![structure] | ![educt] |
| W.2 | ![structure] | ![educt] |

1-benzoyl-3-[1-hydroxy-1-phenylmeth-(Z)-ylidene]-2-oxo-2,3-dihydro-1H-indole-5-sulphonic acid esters are prepared according to Methods D and E.

| # | structure | educt |
|---|-----------|-------|
| E.1 | 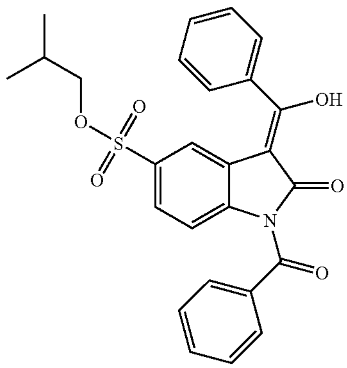 | |
| E.2 | 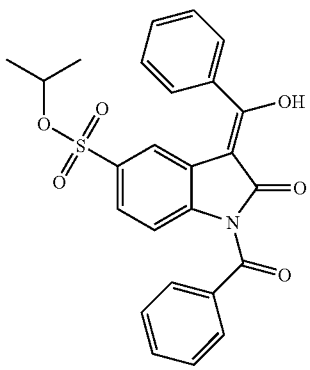 | |

2-oxo-3-[1-phenyl-1-phenylaminometh-(Z)-ylidene]-2,3-dihydro-1H-indole-5-sulphonic acid esters are prepared according to Method G.

EXAMPLES 112-116

| Ex. | structure | $t_{Ret}$ [min] | $UV_{max}$ [nm] | $[M+H]^+$ |
|-----|-----------|-----------------|------------------|-----------|
| 112 | 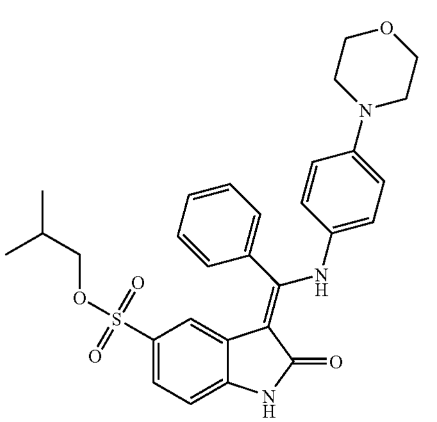 | 2.32 | 381 | 534.2 |

| Ex. | structure | $t_{Ret}$ [min] | $UV_{max}$ [nm] | $[M + H]^+$ |
|---|---|---|---|---|
| 113 | 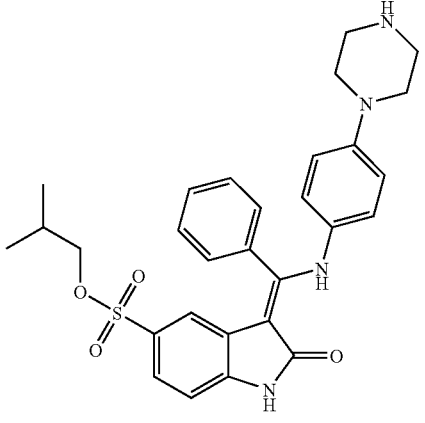 | 1.69 | 385 | 533.3 |
| 114 | 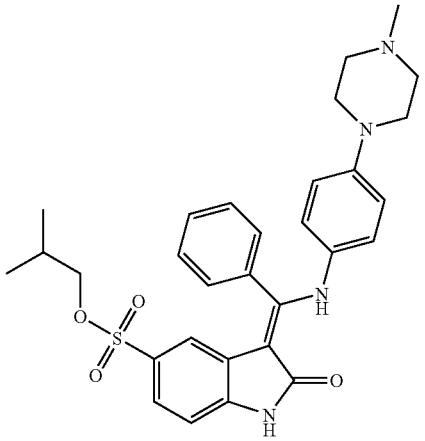 | 1.68 | 380 | 547.2 |
| 115 | 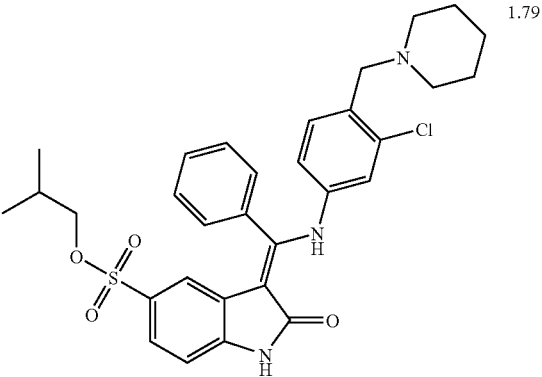 | 1.79 | 380 | 580.3 |

| Ex. | structure | $t_{Ret}$ [min] | $UV_{max}$ [nm] | $[M+H]^+$ |
|---|---|---|---|---|
| 116 | 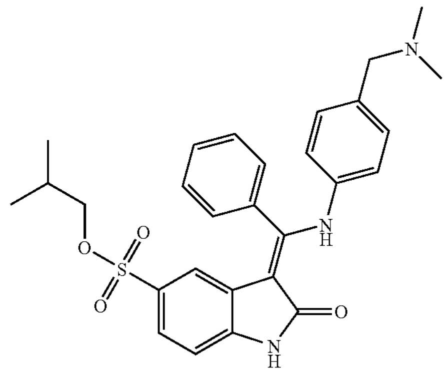 | 1.65 | 380 | 506.2 |

ABBREVIATIONS USED

DMAP N,N-dimethylaminopyridine
DMF N,N-dimethylformamide
DMSO dimethylsulphoxide
EtOAc ethyl acetate
h hour
HCl hydrochloric acid
HPLC high pressure liquid chromatography
M molar
min minute
mL millilitre
MS mass spectrometry
N normal
NMP N-methylpyrrolidinone
NMR nuclear resonance spectroscopy
Ph Phenyl
RP reversed phase
RT ambient temperature
TBTU O-benzotriazol-1-yl-N,N,N',N'-tetramethyluronium tetrafluoroborate
tert tertiary
THF tetrahydrofuran
HPLC Methods
  HPLC: Agilent 1100 Series
  MS: Agilent LC/MSD SL (LCMS1: 1100 series LC/MSD)
  Column: Waters, Xterra MS C18, 2.5 µm, 2.1×30 mm, Part. No. 186000592
  Solvent:
    A: H$_2$O (Millipore purified purest water) with 0.1% HCOOH
    B: acetonitrile (HPLC grade)
  Detection: MS: Positive and negative
  Mass range: 120-900 m/z
  Fragmenter: 120
  Gain EMV: 1
  Threshold: 150
  Stepsize: 0.25
  UV: 254 nm
  Bandwide: 1 (LCMS1: 2)
  Reference: off
  Spectrum: Range: 250-400 nm
  Range step: 1.00 nm
  Threshold: 4.00 mAU
  Peakwidth: <0.01 min (LCMS1: >0.05 min)
  Slit: 1 nm (LCMS 1: 2 nm)
  Injection: Inj. Vol.: 5 µL
  Inj. mode: Needle wash
  Separation: Flow: 1.10 mL/min
  Column temp.: 40° C.
  Gradient: 0 min 5% solvent B
    0-2.5 min 5%->95% solvent B
    2.50-2.80 min 95% solvent B
    2.81-3.10 min 95%->5% solvent B The following Examples describe the biological activity of the compounds according to the invention without restricting the invention to these Examples.

As demonstrated by DNA staining followed by FACS or Cellomics Array Scan analysis, the inhibition of proliferation brought about by the compounds according to the invention is mediated above all by errors in chromosome segregation. Because of the accumulation of faulty segregations, massive polyploidia occurs which may finally lead to inhibition of proliferation or even apoptosis. On the basis of their biological properties the compounds of general formula (I) according to the invention, their isomers and the physiologically acceptable salts and polymorphs thereof are suitable for treating diseases characterised by excessive or abnormal cell proliferation.

Example Aurora-B Kinase Assay

A radioactive enzyme inhibition assay was developed using Baculovirus-expressed recombinant human Aurora B wild-type protein equipped at the N-terminal position with a histidine6) epitope (His-), which is obtained from infected insect cells (SF21) and purified.

Expression and Purification

For this, 300×10$^6$ SF21 cells in SF-900II insect cell medium (Invitrogen) are incubated for example with a suitable amount of Baculovirus solution for 1 h at 27° C. (Fernbach flask agitator, 50 rpm). Then 250 ml SF-900 II medium is added and agitated for 3 days (100 rpm, 27° C.). Three hours before harvesting, okadaic acid (C$_{44}$H$_{68}$O$_{13}$, Calbiochem #495604) is added to the culture (final concentration 0.1 µM) in order to stabilise phosphorylation sites on recombinant Aurora B. The cells are pelleted by centrifugation (1000 rpm, 5 min, 4° C.), the supernatant is discarded and the pellet is frozen in liquid nitrogen. The pellet is thawed (37° C., 5 min) and resuspended in lysis buffer. 40 mL lysis buffer (25 mM Tris/Cl, 10 mM MgCl$_2$, 300 mM NaCl, 20 mM imidazole, pH 8.0, 0.07% 2-mercaptoethanol and Protease-Inhibitor-Complete from Roche Diagnostics) is used for 200 mL of volume of the starting culture. After two rapid freezing/thawing cycles (liquid nitrogen at 37° C.), the lysate is kept on ice for 30 min, then incubated (2 h, 4° C.) with washed Ni-NTA beads (Ni-NTA Superflow Beads, 4 mL per 200 mL of starting culture) and placed in an Econo-Pac column (Biorad #732-1010). Five washes with in each case 10 column volumes of washing buffer (25 mM Tris/Cl, 10 mM $MgCl_2$, 1000 mM NaCl, 20 mM imidazole, pH 8.0, 0.07% 2-mercaptoethanol and Protease-Inhibitor-Complete from Roche Diagnostics) precede the elution in 8 ml (per 200 ml of starting culture) elution buffer (25 mM Tris/Cl pH 8.0, 300 mM NaCl, 10 mM $MgCl_2$, 0.03% Brij-35, 10% glycerol, 0.07% 2-mercaptoethanol, 400 mM imidazole). The combined eluate fractions are desalinated using a Sephadex G25 column and transferred into freezing buffer (50 mM tris/Cl pH 8.0, 150 mM NaCl, 0.1 mM EDTA, 0.03% Brij-35, 10% glycerol, 1 mM DTT).

Kinase Assay

Test substances are placed in a polypropylene dish (96 wells, Greiner #655 201), in order to cover a concentration frame of 10 μM-0.0001 μM. The final concentration of DMSO in the assay is 5%. 30 μL of protein mix (50 mM tris/Cl pH 7.5, 25 mM $MgCl_2$, 25 mM NaCl, 167 μM ATP, 200 ng His-Aurora B in freezing buffer) are pipetted into the 10 μl of test substance provided in 25% DMSO and this is incubated for 15 min at RT. Then 10 μL of peptide mix (100 mM tris/Cl pH 7.5, 50 mM $MgCl_2$, 50 mM NaCl, 5 μM NaF, 5 μM DTT, 1 μCi gamma-P33-ATP [Amersham], 50 μM substrate peptide [biotin-EPLERRLSLVPDS or multimers thereof, or biotin-EPLERRLSLVPKM or multimers thereof, or biotin-LRRWSLGLRRWSLGLRRWSLGLRRWSLG]) are added. The reaction is incubated for 75 min (ambient temperature) and stopped by the addition of 180 μL of 6.4% trichloroacetic acid and incubated for 20 min on ice. A multiscreen filtration plate (Millipore, MAIP NOB 10) is equilibrated first of all with 100 μL 70% ethanol and then with 180 μL trichloroacetic acid and the liquids are eliminated using a suitable suction apparatus. Then the stopped kinase reaction is applied. After 5 washing steps with 180 μL 1% trichloroacetic acid in each case the lower half of the dish is dried (10-20 min at 55° C.) and 25 μL scintillation cocktail (Microscint, Packard # 6013611) is added. Incorporated gamma-phosphate is quantified using a Wallac 1450 Microbeta Liquid Scintillation Counter. Samples without test substance or without substrate peptide are used as controls. $IC_{50}$ values are obtained using Graph Pad Prism software.

The anti-proliferative activity of the compounds according to the invention is determined in the proliferation test on cultivated human tumour cells and/or in a cell cycle analysis, for example on NCI—H460 tumour cells. In both test methods the compounds exhibit good to very good activity, i.e. for example an EC50 value in the NCI—H460 proliferation test of less than 5 μmol/L, generally less than 1 μmol/L.

Measurement of the inhibition of proliferation on cultivated human tumour cells To measure proliferation on cultivated human tumour cells, cells of lung tumour cell line NCI—H460 (obtained from American Type Culture Collection (ATCC)) are cultivated in RPMI 1640 medium (Gibco) and 10% foetal calf serum (Gibco) and harvested in the log growth phase. Then the NCI—H460 cells are placed in 96-well flat-bottomed plates (Falcon) at a density of 1000 cells per well in RPMI 1640 medium and incubated overnight in an incubator (at 37° C. and 5% $CO_2$). The active substances are added to the cells in various concentrations (dissolved in DMSO; DMSO final concentration: 0.1%). After 72 hours incubation 20 μl AlamarBlue reagent (AccuMed International) is added to each well, and the cells are incubated for a further 5-7 hours. After incubation the colour change of the AlamarBlue reagent is determined in a Wallac Microbeta fluorescence spectrophotometer. $EC_{50}$ values are calculated using Standard Levenburg Marquard algorithms (GraphPad-Prizm).

Cell cycle analyses are carried out for example using FACS analyses (Fluorescence Activated Cell Sorter) or by Cellomics Array Scan (CellCycle Analysis).

FACS Analysis

Propidium iodide (PI) binds stoichiometrically to double-stranded DNA, and is thus suitable for determining the proportion of cells in the G1, S, and G2/M phase of the cell cycle on the basis of the cellular DNA content. Cells in the G0 and G1 phase have a diploid DNA content (2N), whereas cells in the G2 or mitosis phase have a 4N DNA content.

For PI staining, for example, $1.75 \times 10^6$ NCI—H460 cells are seeded onto a 75 cm cell culture flask, and after 24 h either 0.1% DMSO is added as control or the substance is added in various concentrations (in 0.1% DMSO). The cells are incubated for 42 h with the substance or with DMSO. Then the cells are detached with trypsin and centrifuged. The cell pellet is washed with buffered saline solution (PBS) and the cells are then fixed with 80% ethanol at −20° C. for at least 2 h. After another washing step with PBS the cells are permeabilised with Triton X-100 (Sigma; 0.25% in PBS) on ice for 5 min, and then incubated with a solution of propidium iodide (Sigma; 10 μg/ml) and RNAse (Serva; 1 mg/mLl) in the ratio 9:1 for at least 20 min in the dark.

The DNA measurement is carried out in a Becton Dickinson FACS Analyzer, with an argon laser (500 mW, emission 488 nm); data are obtained and evaluated using the DNA Cell Quest Programme (BD).

Cellomics Array Scan

NCI—H460 cells are seeded into 96-well flat-bottomed dishes (Falcon) in RPMI 1640 medium (Gibco) with 10% foetal calf serum (Gibco) in a density of 2000 cells per well and incubated overnight in an incubator (at 37° C. and 5% $CO_2$). The active substances are added to the cells in various concentrations (dissolved in DMSO; DMSO final concentration: 0.1%). After 42 h incubation the medium is suction filtered, the cells are fixed for 10 min with 4% formaldehyde solution and Triton X-100 (1:200 in PBS) at RT and simultaneously permeabilised, and then washed twice with a 0.3% BSA solution (Calbiochem). Then the DNA is stained by the addition of 50 μL/well of 4',6-diamidino-2-phenylindole (DAPI; Molecular Probes) in a final concentration of 300 nM for 1 h at RT, in the dark. The preparations are then carefully washed twice with PBS, the plates are stuck down with black adhesive film and analysed in the Cellomics ArrayScan using the CellCycle BioApplication programme and visualised and evaluated using Spotfire.

The substances of the present invention are Aurora kinase inhibitors. On the basis of their biological properties the new compounds of general formula (I), their isomers and the physiologically acceptable salts thereof are suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy).

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus, small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, giant cell tumour, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypemephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma; vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors such as for example PLK-inhibitors as disclosed in WO03/020722 and WO2004/076454, anti-angiogenic substances, steroids or antibodies.

The compounds of general formula (1) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortinsone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example platelet derived growth factor and hepatocyte growth factor, inhibitors are for example growth factor antibodies, growth factor receptor antibodies and tyrosinekinase inhibitors, such as for example gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Suitable preparations include for example tablets, capsules, suppositories, solutions,—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) Tablets | per tablet |
|---|---|
| active substance according to formula (1) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance according to formula (1) | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance according to formula (1) | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of formula (1),

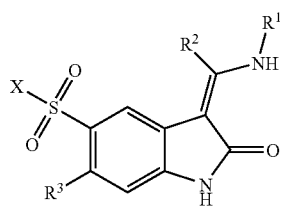

wherein

X denotes —$NR^4R^5$ or —$OR^5$; and $R^1$ denotes a group, optionally substituted by one or more $R^6$, selected from among $C_{6-15}$aryl and 5-15 membered heteroaryl; and $R^2$ denotes a group, optionally substituted by one or more $R^6$, selected from among $C_{3-10}$cycloalkyl, 3-8 membered heterocycloalkyl, $C_{6-15}$aryl and 5-15 membered heteroaryl; and $R^3$ denotes hydrogen or a group selected from among $R^a$, $R^b$ and $R^a$ substituted by one or one or more identical or different $R^b$ and/or $R^c$; and $R^4$ denotes $C_{1-6}$alkyl; and $R^5$ denotes hydrogen or a group, optionally substituted by one or more $R^a$ and/or $R^b$, selected from among $C_{1-6}$alkyl, $C_{3-10}$cycloalkyl, $C_{4-14}$cycloalkylalkyl, 3-8 membered heterocycloalkyl, 4-14 membered heterocycloalkylalkyl and 6-16 membered heteroarylalkyl; or $R^4$ and $R^5$ together with the nitrogen atom to which they are linked form a heterocycloalkyl or heteroaryl ring, wherein this ring may optionally also contain one or more identical or different additional heteroatoms selected from among nitrogen, oxygen and sulphur, and which may optionally be substituted by one or more identical or different suitable $R^e$ and/or $R^f$; and $R^6$ denotes a group selected from among $R^a$, $R^b$ and $R^a$ substituted by one or one or more identical or different $R^b$ and/or $R^c$; and each $R^a$ is independently of one another selected from among $C_{1-6}$alkyl, $C_{3-10}$cycloalkyl, $C_{4-16}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl; and each $R^b$ is a suitable group, each independently selected from among =O, —$OR^c$, $C_{1-3}$haloalkyloxy, —$OCF_3$, =S, —$SR^c$, =$NR^c$, =$NOR^c$, —$NR^cR^c$, halogen, —$CF_3$, —CN, —NC, —OCN, —SCN, —$NO_2$, —S(O)$R^c$, —S(O)$_2R^c$, —S(O)$_2OR^c$, —S(O)$NR^cR^c$, —S(O)$_2NR^cR^c$, —OS(O)$R^c$, —OS(O)$_2R^c$, —OS(O)$_2OR^c$, —OS(O)$_2NR^cR^c$, —OS(O)$NR^cR^c$, —C(O)$R^c$, —C(O)$OR^c$, —C(O)$NR^cR^c$, —CN($R^f$)$NR^cR^c$, —CN(OH)$R^c$, —CN(OH)$NR^cR^c$, —OC(O)$R^c$, —OC(O)$OR^c$, —OC(O)$NR^cR^c$, —OCN($R^f$)$NR^cR^c$, —N($R^f$)C(O)$R^c$, —N($R^f$)C(S)$R^c$, —N($R^f$)S(O)$_2R^c$, —N($R^f$)C(O)$OR^c$, —N($R^f$)C(O)$NR^cR^c$, —[N($R^f$)C(O)]$_2R^c$, —N[C(O)]$_2R^c$, —N[C(O)]$_2OR^c$, —[N(R)C(O)]$_2OR^c$ and —N($R^f$)CN($R^f$)$NR^cR^c$; and each $R^c$ independently of one another is hydrogen or a group optionally substituted by one or more identical or different $R^d$ and/or $R^e$ selected from among $C_{1-6}$alkyl, $C_{3-10}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl; and each $R^d$ independently of one another is hydrogen or a group optionally substituted by one or more identical or different $R^e$ and/or $R^f$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl; and each $R^e$ is a suitable group and each independently selected from among =O, —$OR^f$, $C_{1-3}$haloalkyloxy, —$OCF_3$, =S, —$SR^f$, =$NR^f$, =$NOR^f$, —$NR^fR^f$, halogen, —$CF_3$, —CN, —NC, —OCN, —SCN, —$NO_2$, —S(O)$R^f$, —S(O)$_2R^f$, —S(O)$_2OR^f$, —S(O)$NR^fR^f$, —S(O)$_2NR^fR^f$, —OS(O)$R^f$, —OS(O)$_2R^f$, —OS(O)$_2OR^f$, —OS(O)$_2NR^fR^f$, —C(O)$R^f$, —C(O)$OR^f$, —C(O)$NR^fR^f$, —CN($R^g$)$NR^fR^f$, —CN(OH)$R^f$, —C(NOH)$NR^fR^f$, —OC(O)$R^f$, —OC(O)$OR^f$, —OC(O)$NR^fR^f$, —OCN($R^g$)$NR^fR^f$, —N($R^g$)C(O)$R^f$, —N($R^g$)C(S)$R^f$, —N($R^g$)S(O)$_2R^f$, —N($R^d$)C(O)$OR^f$, —N($R^g$)C(O)$NR^fR^f$, and —N($R^g$)CN($R^f$)$NR^fR^f$; and each $R^f$ independently of one another is hydrogen or a group optionally substituted by one or more identical or different $R^g$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl; and each $R^g$ independently of one another is hydrogen, $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl, optionally in the form of a tautomer, a racemate, an enantiomer, a diastereomer or a mixture of any of the foregoing or optionally a pharmacologically acceptable acid addition salt thereof, with the proviso that 3-Z-[1-(4-(piperidin-1-yl-methyl)-anilino)-1-phenyl-methylene]-5-(N-buty-N-methyl-aminosulphonyl)-2-indolinone and 3-Z-[1-(4-(dimethylaminomethyl)-anilino)-1-phenyl-methylene]-5-aminosulphonyl-2-indolinone are excluded.

2. The compound according to claim 1, wherein $R^1$ denotes phenyl.

3. The compound according to claim 1, wherein $R^2$ denotes phenyl, cyclohexyl or pyridyl.

4. The compound according to claim 1, wherein $R^2$ denotes unsubstituted phenyl.

5. The compound according to claim 1, wherein X denotes —$NR^4R^5$.

6. A pharmaceutical preparation, comprising as an active substance one or more compounds of formula (1) according to claim 1 or the physiologically acceptable salt thereof optionally in combination with conventional excipients or carriers.

7. The pharmaceutical preparation of claim 6 further comprising at least one other cytostatic or cytotoxic active substance, different from a compound of formula (1).

* * * * *